United States Patent [19]

Loughrey et al.

[11] Patent Number: 5,399,331
[45] Date of Patent: Mar. 21, 1995

[54] METHOD FOR PROTEIN-LIPOSOME COUPLING

[75] Inventors: Helen C. Loughrey; Pieter R. Cullis, both of Vancouver; Marcel B. Bally, Bowen Island; Lewis S. Choi, Burnaby, all of Canada

[73] Assignee: The Liposome Company, Inc., Princeton, N.J.

[21] Appl. No.: 946,806

[22] Filed: Sep. 17, 1992

Related U.S. Application Data

[63] Continuation of Ser. No. 412,779, Sep. 26, 1989, abandoned, which is a continuation-in-part of Ser. No. 370,650, Jun. 23, 1989, Pat. No. 5,059,421, which is a continuation-in-part of Ser. No. 941,913, Dec. 15, 1986, Pat. No. 4,885,172, which is a continuation-in-part of Ser. No. 811,037, Dec. 18, 1985, abandoned, which is a continuation-in-part of Ser. No. 749,161, Jun. 26, 1985, abandoned, and Ser. No. 759,419, Jul. 26, 1985, Pat. No. 4,880,635.

[51] Int. Cl.⁶ ............................................. A61K 37/22
[52] U.S. Cl. ................................... 424/450; 424/417; 424/418
[58] Field of Search .................. 424/450, 417, 418

[56] References Cited

U.S. PATENT DOCUMENTS

| | | | |
|---|---|---|---|
| 4,235,871 | 11/1980 | Papahadjopoulos et al. | 424/19 |
| 4,522,803 | 6/1985 | Lenk et al. | 424/1.1 |
| 4,721,612 | 1/1988 | Janoff et al. | 424/1.1 |
| 4,743,560 | 5/1988 | Campbell et al. | 436/501 |
| 4,885,172 | 12/1989 | Bally | 424/417 |

FOREIGN PATENT DOCUMENTS

| | | | |
|---|---|---|---|
| 86/00238 | 1/1986 | WIPO . | |
| 86/04232 | 7/1986 | WIPO | A61K 9/00 |
| 87/02219 | 4/1987 | WIPO . | |

OTHER PUBLICATIONS

Allison, et al., "Liposomes as immunological adjuvants,": 1974, Nature, vol. 252, p.252.
Bangham, et al.; "Diffusion of Univalent Ions Across the Lamellae of Swollen Phospholipids", 1965; J. Mol. Biol., 13:238–252.
Barbet, et al., "Monoclonal antibody Covalently Coupled to Liposomes: Specific Targeting to Cells," J. Supramol. Struct. Cell Biochem., 16:243–258.
Bayer, et al., "Affinity Cytochemistry: The Localization of Lectin and Antibody Receptors on Erythrocytes via the Avidin–Biotin Complex," 1976, FEBS Letters, 68, pp. 240–244.
Boyum, "Isolation of Leucocytes from Human Blood," 1968, Scand. J. Clin. Lab, Invest., 21, Supp. 97,9.
Bragman, et al., "Cytotoxicity of Antibody–Directed Liposomeds that Recognize Two Receptors on K562 cells", 1984, JNCI vol. 73(1):127–131.
Bredehorst, et al., "Effect of covalent Attachment of Immunoglobulin Fragements on Liposomal Integrity," 1986, J. Natl. Cancer Inst., 73:5693–5698.
Carlsson, et al., "Protein Thiolation and Reversible Protein–Protein Conjugation",: 1978, Biochem. J. 173: 723–737.
Deamer, et al., "Liposome Preparation: Methods and Mechanisms," 1983, Chapter 1, pp. 27–51.
Fiske, et al., "The Colorimetric Determination of Phosphourus", 1925, J. Biol. Chem., 66:375–400.
Forssen, et al., "Improved Therapeutic Benefits of Doxorubicin by Entrapment in Anionic Liposomes", 1983, Cancer Res., 43:546.

(List continued on next page.)

Primary Examiner—D. Gabrielle Phelan
Attorney, Agent, or Firm—Kenneth B. Rubin

[57] ABSTRACT

This invention relates to a method for synthesizing a substantially pure reactive lipid including, for example, N-[4-(p-maleimidophenyl)-butyryl]phosphatidylethanolamine (MPB-PE) and related compositions. The compositions of the present invention are useful as coupling agents and may be incorporated into liposomes and subsequently coupled to proteins, cofactors and a number of other molecules. A preferred coupling method is also disclosed as are protein conjugates.

25 Claims, 7 Drawing Sheets

OTHER PUBLICATIONS

Gabizon, et al., "Liposomes as in Vivo Carriers of Adriamycin:Reduced Cardiac Uptake and Preserved Antitumor Activity in Mice", 1982, Cancer Res. 42–4734.

Goundalker et al., "Covalent binding of antibodies to liposomes using a novel lipid drivative," 1984, J. Pharm. Pharmacol., 36:465–466.

Gregoriadis, "Targeting of drugs with molecules, cells and liposomes," 1983, Trends Pharmacol Sci., 4:304–307.

Health, et al., "Antibody-targeted liposomes: Increase in specific toxicity of methotrexate-aspartate", 1983, Proc. Natl. Acad. Sci, SA, 80:1377–1381.

Heath, et al., "Covalent Attachment of Immunoglobulins to Lipsomes via Glycosphingolipids", 1981, BBA 640:66–81.

Ho, et al., "Interactions of Antigen-Sensitized Liposomes with Immobilized Antibody: A Homogeneous Solid-Phase Immunoliposome Assay", 1985, J. Immunol. vol. 134, No. 6.:4035–4040.

Howard, et al., "A Human T Lymphocyte Differentiation Market Defined by Monoclonal antibodies that Block E-Rosette Formation", 1981, J. Immunol. vol. 126, No. 6:2117–2122.

Huang, et al., "Characterization of Antibody Covalently Coupled to Liposomes", 1982, BBA, 716:140–150.

Huang, et al., "Interations of Immunoliposomes with Target Cells". 1983, J. Biol. Chem, vol. 258, No. 22,pp. 14034–14040.

Ishimori, et al., "Liposome Immune Lysis Assay (LILA):a Simple Method to Measure Anti-Protein Antibody using Protein Antigen-Bearing Liposomes", 1984, J. Immunol. Methods, 75:351-360.

Leserman, et al. "Targeting to cells of fluorescent liposomes covalently coupled with monoclonal antibody or protein A," 1980, Nature, 288:602–604.

Leserman, et al., "Covalent coupling of Monoclonal Antibodies and Protein A to Liposomes: Specific Interaction with Cells in Vitro and in Vivo",: Liposome Technology, III, 1984, CRC Press, Inc., CA., pp. 29–40.

Loughrey, et al., "A non-covalent method of attaching antibodies to liposomes", 1987, BBA, 901:157–160.

Martin, et al., "Irreversible Coupling of Immunoglobulin Freagments to Preformed Vesciles," 1982, J. Biol. Chem., 257, pp. 286–288.

Martin et al., "immunospecific Targeting of Liposomes to Cells: A Novel and Efficient Method for Covalent Attachement of Fab' Gragments via Disulfide Bonds", 1981, Biochemistry, 20 4220–4238.

Martin, et al., "Binding characteristics of Antibody-Bearing Liposomes", 1985, Ann. NY Acad. Sci. Col 446;443–456.

Papahadjopoulos, et al., "Phospholipid Model Membranes", 1967: Biochim. Biophys. Acta., 1345:624–638.

Rahman, et al., "Doxorubicin-induced Chronic Cardiotoxicity and its Protection by Liposomal Administration", 1982; Cancer Res. 42:1817.

Rahman, et al., "In Vivo Cell Targeting by Liposomes Containing Glycolipids," 1979, J. Cell Biol., MF1509.

Sedlack, et al., "Estimation of Total, Protein-Bound, and Nonprotein Sulfhydryl Groups in Tissue with Ellman's Reagent", 1968, Anal. Biochem. 25:192–205.

Sharkey, et al., "Targeting of Antibody Coated Liposomes to Tumor Cells producing carcinoembyonic antigen", 1979, Immunotherapy #4557.

Stashenko, et al., "Characterization of a huyman B Lymphocyte-Specific Antigen[1]" 1980, J. Immunol., vol. 125 No. 4:1678–1685.

Urdal et al., "Tumor-associated Ganglio-N-triosylceramide", 1984 J. Biol Chem., 255:10509–10516.

Wolff, et al., "The Use of Monocloanl Anti-Thy, IgG,1 for the Targeting of Liposomes to AKR-A cells in vitro and in vivo," 1984, BBA 802:259–273.

Bayer, et al., "Methodology Involved in Biotin-Conjugated Phospholipids, Glycolipids, and Gangliosides," Liposome Technology, vol. III, Targeted Drug Delivery and Biological Interaction, 1986, Gregory Gregoriadis, ed., Cp 9, p. 127135.

| MIN | MAX | COUNT | PERCENT | MEAN | SD | I HPCV |
|---|---|---|---|---|---|---|
| 1 2.705 | 1023. | 70 | 1.4 | 4.159 | 2.788 | 45.8 |

| MIN | MAX | COUNT | PERCENT | MEAN | SD | I HPCV |
|---|---|---|---|---|---|---|
| 1 2.705 | 1023. | 1015 | 20.3 | 22.11 | 3.89 | 2.57 |

METHOD FOR PROTEIN-LIPOSOME COUPLING

This is a continuation of application Ser. No. 412,779, filed on Sep. 26, 1989, now abandoned, which is a continuation-in-part application of patent application Ser. No. 370,650, filed Jun. 23, 1989, now U.S. Pat. No. 5,059,421, which is a continuation-in-part application of patent application Ser. No. 941,913, filed Dec. 15, 1986, now U.S. Pat. No. 4,885,172, which is a continatuion-in-part application of patent application Ser. No. 811,037, filed Dec. 18, 1985, now abandoned which is a continuation-in-part application of patent application Ser. No. 749,161, filed Jun. 26, 1985, now abandoned and patent application Ser. No. 759,419, filed Jul. 26, 1985, now U.S. Pat. No. 4,880,635.

FIELD OF THE INVENTION

This invention relates to a method for synthesizing a substantially pure reactive lipid including, for example, N-[4-(p-maleimidophenyl)-butyryl]phosphatidylethanolamine (MPB-PE) and related compositions. The compositions of the present invention are useful as coupling agents and may be incorporated into liposomes and subsequently coupled to proteins, cofactors and a number of other molecules.

The present invention further relates to lipids modified with SMPB and related crosslinking agents and the liposomes obtained by incorporating substantially pure reactive lipid, including MPB-PE, and related coupling compositions into lipids.

Protein-liposome conjugates of the present invention may be used for therapeutic and diagnostic targeting of liposomes.

Protein-liposome conjugates of the present invention may have a transmembrane potential across their membranes, and may be dehydrated. In addition, the conjugates may contain ionizable bioactive agents, for example antineoplastic agents, and may be used in diagnostic assays.

BACKGROUND OF THE INVENTION

Liposomes are completely closed structures comprising lipid bilayer membranes containing an encapsulated aqueous volume. Liposomes may contain many concentric lipid bilayers separated by an aqueous phase (multilamellar vesicles or MLVs), or alternatively, they may comprise a single membrane bilayer (unilamellar vesicles). The lipid bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase. The basic structure of liposomes may be made by a variety of techniques known in the art.

Liposomes have typically been prepared using the process of Bangham et al., (1965 *J. Mol. Biol.*, 13: 238-252), whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form. The aqueous phase entrapped within the liposomes may contain bioactive agents, for example drugs, hormones, proteins, dyes, vitamins, or imaging agents, among others.

Liposomes may be reproducibly prepared using a number of currently available techniques. The types of liposomes which may be produced using a number of these techniques include small unilamellar vesicles (SUVs) [See Papahadjapoulous and Miller, *Biochem. Biophys. Acta.*, 135, p. 624–638 (1967)], reverse-phase evaporation vesicles (REV) [See U.S. Pat. No. 4,235,871 issued Nov. 25, 1980], stable plurilamellar vesicles (SPLV) [See U.S. Pat. No. 4,522,803, issued Jun. 11, 1985], and large unilamellar vesicles produced by an extrusion technique as described in copending U.S. patent application Ser. No. 622,690, filed Jun. 20, 1984, Cullis et.al., entitled "Extrusion Technique for Producing Unilamellar Vesicles", relevant portions of which are incorporated herein by reference.

Liposomes may be used as carriers for a wide variety of materials, for example drugs, cosmetics, diagnostic reagents and bioactive compounds, among others. Liposome compositions to which proteins are conjugated may be designed for both diagnostic and in vivo uses. For example, the ability to produce an antibody-directed vesicle would be a distinct advantage over similar undirected systems (Gregoriadis, G., *Trends Pharmacol Sci*, 4, p. 304–307, 1983), as would the targeting of a specific receptor or other cell surface feature. Useful applications of these protein-liposome conjugates would be in the selective targeting of cytotoxic compounds entrapped in vesicles to circulating tumor cells (Wolff et.al., *Biochim. Biophys. Acta*, 802, p. 259–273 1984), or applications of these immunoglobulin-associated vesicles in the development of diagnostic assays. Further applications could result from the targeting of a specific protein-receptor interaction for delivery of active agent to a specific site in a patient. Indeed, protein conjugated liposomes theoretically could be used to target the delivery of any active agent to a site in the patient's system to which the protein will bind. Numerous techniques for the conjugation of proteins to liposomes have already been developed for a variety of purposes including the targeting of drugs via immunoliposomes [See Leserman, et al., *Nature*, 288, 602 (1980), Heath, et al., *Proc. Natl. Acad. Sci. USA*, 80, 1377 (1983) and Huang, et al., *J. Biol. Chem.*, 258, 14034 (1983)], diagnostic protocols [See Ishimori, et al., *J. Immunol. Methods*, 75, 351 (1984) and Rodney, et al., *J. Immunol.*, 134, 4035 (1985)] and liposomal vaccines [See Allison, et al., *Nature*, 252, 252 (1974)].

Liposomes may be covalently coupled to proteins, antibodies and immunoglobulins. Heath et.al. (*Biochim. Biophys. Acta.*, 640, p. 66–81, 1981), describe the covalent attachment of immunoglobulins to liposomes containing glycosphingolipid. Leserman et. al. (*Liposome Technology*, III, 1984, CRC Press, Inc., California, p. 29–40; *Nature*, 288, p. 602–604, 1980) and Martin et. al., (*J. Biol. Chem.*, 257, p. 286–288, 1982) have described procedures whereby thiolated IgG or protein A is covalently attached to lipid vesicles, and thiolated antibodies and Fab' fragments are attached to liposomes, respectively. These protocols and various modifications (Martin et.al, *Biochemistry*, 20, p. 4229–4238, 1981; and Goundalkar et.al., *J. Pharm. Pharmacol.*, 36, p. 465–466, 1984) represent the most versatile approaches to coupling. Avidin-coupled and avidin and biotinyl-coupled phospholid liposomes containing actinomycin D have successfully targeted tumor cells expressing ganglio-N-triosylceramide (Urdal et.al., *J. Biol. Chem.*, 255, p. 10509–10516, 1980). Huang et.al. (*Biochim. Biophys. Acta.*, 716, p. 140–150, 1982) demonstrate the binding of mouse monoclonal antibody to the major histocompatibility antigen H-2 (K), or goat antibody to the major glycoprotein of Molony Leukemia Virus, to palmitic acid. These fatty acid modified IgGs were incorporated into liposomes, and the binding of these liposomes to cells expressing the proper antigens characterized. Other in vitro efforts to promote specific binding of liposomes coated with specific immunoglobins have been performed (Sharkey et.al., *Fed. Proc.*, 38, 1089, 1979). In still other coupling studies, Rahman et. al. found that tissue uptake of liposomes could be altered by attachment of glycolipids to the liposomes (*J. Cell Biol.*, 83, p. 268a, 1979).

In accordance with a primary use for liposomes, the entrapment of antineoplastic agents inside liposomal bilayers has resulted in more efficacious therapy as compared to direct administration of the drug. (Forssen et.al., *Cancer Res.*, 43, p. 546, 1983; and Gabizon et.al., *Cancer Res.*, 42, p. 4734, 1982). A major problem with the encapsulation of antineoplastic drugs as well as other agents is that many of these drugs have been found to be rapidly released from liposomes after encapsulation. This is an undesirable effect, in view of the fact that toxicity of many of the antineoplastic agents can be significantly reduced through liposome encapsulation as compared to direct administration. See, for example, Forssen et.al. *Cancer Res.* 43, 546 (1983) and Rahman et.al. *Cancer Res.*, 42, 1817 (1982). In addition, certain pharmacological agents which are favorably delivered in sustained release fashion are not accommodated by standard liposomal delivery systems; many liposomal compositions release the agent too rapidly to provide sustained release delivery.

One answer to the above-described problem is the use of preformed, stable liposomes which maintain the stability and sustained release characteristics of the liposomal system. Liposomal compositions comprising protein-coupled liposomes have produced storage stable liposomes which may be stored stably for an indefinite period, as described in U.S. patent application, Ser. No. 811,037, filed Dec. 18, 1985, entitled "Novel Composition for Targeting, Storing and Loading of Liposomes". These liposomes, which include streptavidin and immunoglobulin coupled to liposomes, may be stored in a dehydrated state, with loading of the liposomes on an "as needed" basis. These protein-coupled liposomes have been loaded with ionizable antineoplastic agents wherein a transmembrane potential is created across the walls of the liposomes and the antineoplastic agent is loaded into the liposomes by means of the transmembrane potential. See, for example, U.S. patent application Ser. No. 749,161, Bally et.al. entitled "Encapsulation of Antineoplastic Agents in Liposomes," filed Jun. 26, 1985 and U.S. patent application Ser. No. 941,913, entitled "Novel Composition for the Targeting, Storing and Loading of Liposomes," filed Dec. 15, 1986, relevant portions of which are incorporated herein by reference.

As explained above, protein-liposome conjugates have many potential applications, ranging from diagnostic systems to the targeting of disease states in vivo. As indicated elsewhere [Loughery, et al., *Biochim. Biophys. Acta*, 901, 157 (1987], the coupling of streptavidin to liposomes results in a flexible basic system which subsequently allows the straightforward conjugation of a variety of proteins.

Covalent attachment of liposomes to antibodies which are directed against cell surface antigens such as those associated with transformed cells, has considerable therapeutic potential. However, at the present time, such targeted liposomal systems have mainly been used for in vitro applications such as in diagnostic assays (Martin and Kung, *Ann. N.Y. Acad. Sci.*, pp. 443–449 (1985). In order to exploit the full potential of antibody targeted carrier systems, as well as other systems, for example liposome-protein coupling and liposome-cofactor coupling, an improved versatile and reliable methodology for coupling should be developed.

To date, no general procedure for attaching proteins, antibodies and other molecules to liposomes is yet available. Leserman, et al. *Nature (London)*, 288, 602–604 (1980) and Barbet, et al., *J. Supramol. Struct. Cell. Biochem.*, 16, 243–258 (1981) have described a procedure wherein a thiolated IgG is covalently attached to liposomes containing N-[3-(2-pyridyldithio)-propionyl]-phosphatidylethanolamine (PDP-PE) via a disulfide bond. A more general version of this procedure was developed by coupling protein A to vesicles (see, for example, Leserman (1980), supra.), which takes advantage of the ability of protein A to bind the Fc protion of IgGs of certain classes. One major limitation of this method is that many monoclonal antibodies are not of the appropriate class.

An alternative to the above approach to coupling is that of Martin and Papahajopoulos, *J. Biol. Chem.*, 257, 286–288 (1982) who developed the technique of covalently attaching antibodies and Fab' fragments to liposomes containing N-[4-(p-maleimidophenyl)-butyryl]-phosphatidylethanolamine (MPB-PE) by formation of a thio-ether linkage with the maleimido group, a linkage which is considerably less susceptible to reducing conditions found in the serum than is the disulfide linkage of the Leserman method. The Martin/Papahajopoulos approach as well as various modifications of this approach [see, for example, Wolff and Gregoriadis, *Biochem. Biophys Acta*, 802, 259 (1984), Martin, et al., *Biochemistry*, 20, 4229 (1981) and Goundalkar, et al., *J. Pharm. Pharmacol.*, 36, 465 (1984) represent the most versatile approaches to coupling currently available.

In this Inethod of cross-linking liposomes to proteins, antibodies, cofactors and other molecules to liposomes, cross-linking agents containing a maleimide group, for example, N-succinimidyl 4-(p-maleimidophenyl)butyrate (SMPB), among others, are used to cross-link phosphatidylethanolamine and other amine containing lipids to thiol containing conjugated molecules, for example, proteins, antibodies, cofactors and other molecules containing reactive thiols. Prior art cross-linking agents, for example SMPB, which are reacted with phosphatidylethanolamine and other lipids according to literature protocols are subject to an opening of the maleimide ring during displacement of the succinimidyl group, resulting in contamination of the reacted product with the ring-opened MPB-lipid derivative. Cross-linking to proteins, antibodies, cofactors and other molecules is less than ideal using the prior art literature protocols. The method of the present invention serves to obviate this problem by providing liposomes comprising substantially pure MPB-PE, i.e., SMPB derivatized phosphatidylethanolamine exhibiting an absence of ring-opened MPB-lipid which is produced using the prior art methods. Liposomes comprising substantially pure MPB-PE may be further reacted with various proteins, for example streptavidin, among others, antibodies, cofactors and other molecules to produce conjugated liposomes of the present invention.

In accordance with a primary aspect of the present invention, i.e., the delivery of bioactive agents to a therapeutic site, the entrapment of antineoplastic agents inside liposomal bilayers has resulted in more efficacious therapy as compared to direct administration of the drug. (Forssen et.al., *Cancer Res.*, 43, p. 546, 1983; and Gabizon et.al., *Cancer Res.*, 42, p. 4734, 1982). A major problem with the encapsulation of antineoplastic drugs as well as other agents is that many of these drugs have been found to be rapidly released from liposomes after encapsulation. This is an undesirable effect, in view of the fact that toxicity of many of the antineoplastic agents can be significantly reduced through liposome encapsulation as compared to direct administration. See, for example, Forssen et.al. *Cancer Res.* 43, 546 (1983) and Rahman et.al. *Cancer Res.*, 42, 1817 (1982). In addition, certain pharmacological agents which are favorably delivered in sustained released fashion are not accommodated by standard liposomal delivery systems; many liposomal compositions release the agent too rapidly to provide sustained release delivery.

In accordance with the present invention, a conjugated liposome made by binding a protein, antibody, cofactor or other molecule to a liposome comprised of an effective amount of substantially pure MPB-PE and related maleimide containing derivatives may be stored stably for an indefinite period, in a dehydrated state, with loading of the liposomes on an "as needed" basis.

It is an object of the present invention to provide a general method for the synthesis of substantially pure MPB-lipid and in particular, substantially pure MPB-PE and related maleimide containing derivatives and related maleimide containing derivatives and related compounds.

It is an additional object of the present invention to provide liposomes comprising substantially pure MPB-PE and related maleimide containing derivatives. Such liposomes may be further reacted with proteins, antibodies, cofactors and other molecules to produce conjugated liposomes.

It is still a further object of the present invention to provide conjugated liposomes of the present invention which have entrapped at least one bioactive agent, such as a drug.

It is still another object of the present invention to provide an efficient coupling technique in combination with stable cross-linkages to produce liposome conjugates which may more efficiently deliver encapsulated materials to cells.

It is yet an additional object of the present invention to provide stable conjugated liposomes which have more efficiently bound protein to the liposome than prior art methods and which can be stored stably for long periods of time.

SUMMARY OF THE INVENTION

In the method of the present invention, phosphatidylethanolamine (PE) or a related liposome forming nucleophilic lipid is reacted with a crosslinking agent having at least one maleimido group and an amine reactive function, for example SMPB, to produce a substantially pure reactive lipid, for example MPB-PE. In the method of the present invention, the reaction of the nucleophilic lipid, for example PE, occurs in the absence of hydrolytic conditions to avoid a ring-opened side product which is produced by following the method of the prior art. After the production of pure reactive lipid, for example, MPB-PE, a thiol-containing conjugated molecule, for example, a protein or other molecule such as an antibody or cofactor, is covalently linked to the reactive lipid to produce a liposome cross-linked with the protein, antibody, cofactor or other molecule. As used herein, such a cross-linked liposome is referred to as a conjugated liposome.

It has surprisingly been discovered that the reaction of SMPB with a nucleophilic liposome forming lipid, for example, PE, utilizing the prior art methodology (conditions which employ methanol, ethanol or other alcohol as solvent under basic conditions) results in the production of a reactive lipid, for example, MPB-PE, plus a substantial amount of a side product in which the maleimide ring is opened by the alcohol ("ring-opened side product"). It has also been discovered that the use of chromatographic and other separation techniques employing alcohols results in the production of a significant amount of ring-opened side product.

In the method of the present invention to produce substantially pure reactive lipid, for example, MPB-PE of the present invention, the following steps are utilized:

1. A crosslinking agent such as SMPB is reacted with a nucleophilic lipid in a solvent containing a non-nucleophilic amine in the absence of a nucleophilic solvent for a period of time sufficient to complete conversion of nucleophilic lipid to reactive lipid such as MPB-PE;
2. After the reaction to form reactive lipid is substantially complete, the solution is diluted with a solvent and washed at least once with water, preferably a saline solution, to remove byproducts; and
3. The solution from (2) is concentrated in vacuo and the solid residue triturated to remove unreacted SMPB and succinimide byproduct to produce a reactive lipid, for example, MBP-lipid.

It is to be noted that substantially pure reactive lipid may also be made by employing steps 1 and 3 sequentially without step 2. Although many of the reactive lipids of the present invention are made using all three steps set forth hereinabove, it is to be understood that certain reactive lipids may be triturated from solution after conversion step 1 to produce substantially pure reactive lipid.

In further steps of the method aspect of the present invention, pure reactive lipid may be recrystallized and subsequently incorporated into liposomes to form reactive liposomes. The reactive liposomes may be reacted with a conjugated molecule, e.g., a thiol-containing protein, antibody, cofactor or a related molecule to produce a conjugated liposome of the present invention. The conjugated liposomes of the present invention may be used for targeting the delivery of a wide variety of bioactive agents or for diagnostic purposes. For example, the application of these conjugates in targeting and diagnostic regimes may be illustrated by the specific binding of such conjugates to lymphocytes via defined biotinated monoclonal antibodies, in a manner which is reflective of the cell distribution of the target antigen [see, for example, Stashenko, et al., *J. Immunol.*, 125, 1678 (1980) and Howard, et al., *J. Immunol.*, 126, 2117 (1981)].

A new protocol for the synthesis of a pure SMPB derivative of a nucleophilic lipid is presented here. Coupling conditions for the conjugation of proteins to liposomes were optimized such that the integrity of the maleimide function of the reactive lipid, for example, MPB-Dipalmitoylphosphatidylethanolamine (MPB-DPPE), was retained. Coupling efficiencies of over 50% are readily achieved under the optimized conditions detailed in the present application. Similar efficiencies have been attained using the prior art methods only in conjunction with higher levels of MPB-EPE in liposomes [5 mole %; see, for example, Bragman, et al., *J. Natl. Cancer Inst.*, 73, 127 (1984)]. The efficient coupling associated with the use of substantially pure reactive lipid, for example, MPB-PE of the present invention, is of particular importance as concentrations of reactive lipid in liposomes of greater than about 2.5 mole % dramatically affect liposome stability [see, for example, Bredehorst, et al., *Biochemistry*, 25, 5693 (1986)].

The present invention is also directed to reactive liposomes comprising at least one substantially pure reactive lipid, for example, MBP-PE, in combination with at least one additional liposome forming lipid. Liposomes of the present invention generally comprise at least about 0.05 mole percent of a substantially pure reactive lipid such as MPB-PE and no greater than about 99.95 mole percent of at least one liposome producing lipid. Conjugated liposomes of the present invention further comprise various proteins, antibodies, cofactors and other molecules which are covalently or noncovalently linked to the liposomes. In one aspect of the present invention, streptavidin is used to form conjugated liposomes of the present invention. These streptavidin coated liposomes rapidly and efficiently bind biotinated proteins and lead to conjugated liposomes which exhibit specific targeting properties in vitro. Such liposomes may be utilized in therapeutic and diagnostic targeting applications.

Liposomes of the present invention may be loaded with a bioactive agent as well as pharmaceutical agents, for example anticancer agents, local anaesthetics, brochodilators, beta-adrenergic blockers, antihypertensive agents, anti-depressants, anti-convulsants, anti-histamines, anti-malarial agents and analgesics among a number of other pharmaceutical agents. To load an active agent into the liposomes of the present invention, any of the methods for loading bioactive agents known to those of ordinary skill in the art may be used. Preferably, however, the liposomes are prepared in such a way as to create a transmembrane potential across their lamellae in response to a concentration gradient. This concentration gradient may be created by either a Na+/K+ potential or a pH gradient (H+). The difference in internal versus external potential is the mechanism which drives the loading of the liposomes with ionizable bioactive agents; delayed loading of preformed liposomes will occur in response to the transmembrane potential.

The liposome conjugates of the present invention may be dehydrated in the presence of one or more protecting sugars, stored in their dehydrated condition, and subsequently rehydrated with retention of the ion gradient and associated ability to accumulate the bioactive agent. In addition, the protein-liposome conjugates of the present invention may be used in diagnostic assays.

BRIEF DESCRIPTION OF THE DRAWINGS

As shown in FIG. 4, the amount of liposomally conjugated protein increased rapidly at pH values greater than 7.0, but resulted in a corresponding rapid degradation of the maleimide group of the reactive lipid. FIG. 5 shows a time course relating streptavidin binding to liposomes to the reactivity of the maleimide lipid. The results indicate that optimal levels of streptavidin conjugated to liposomes (approx. 37 ug/umole of lipid) were obtained with minimal degradation of the maleimide after an incubation period of 8 hours at pH 7.5 and room temperature.

DETAILED DESCRIPTION OF THE INVENTION

Figure 1:
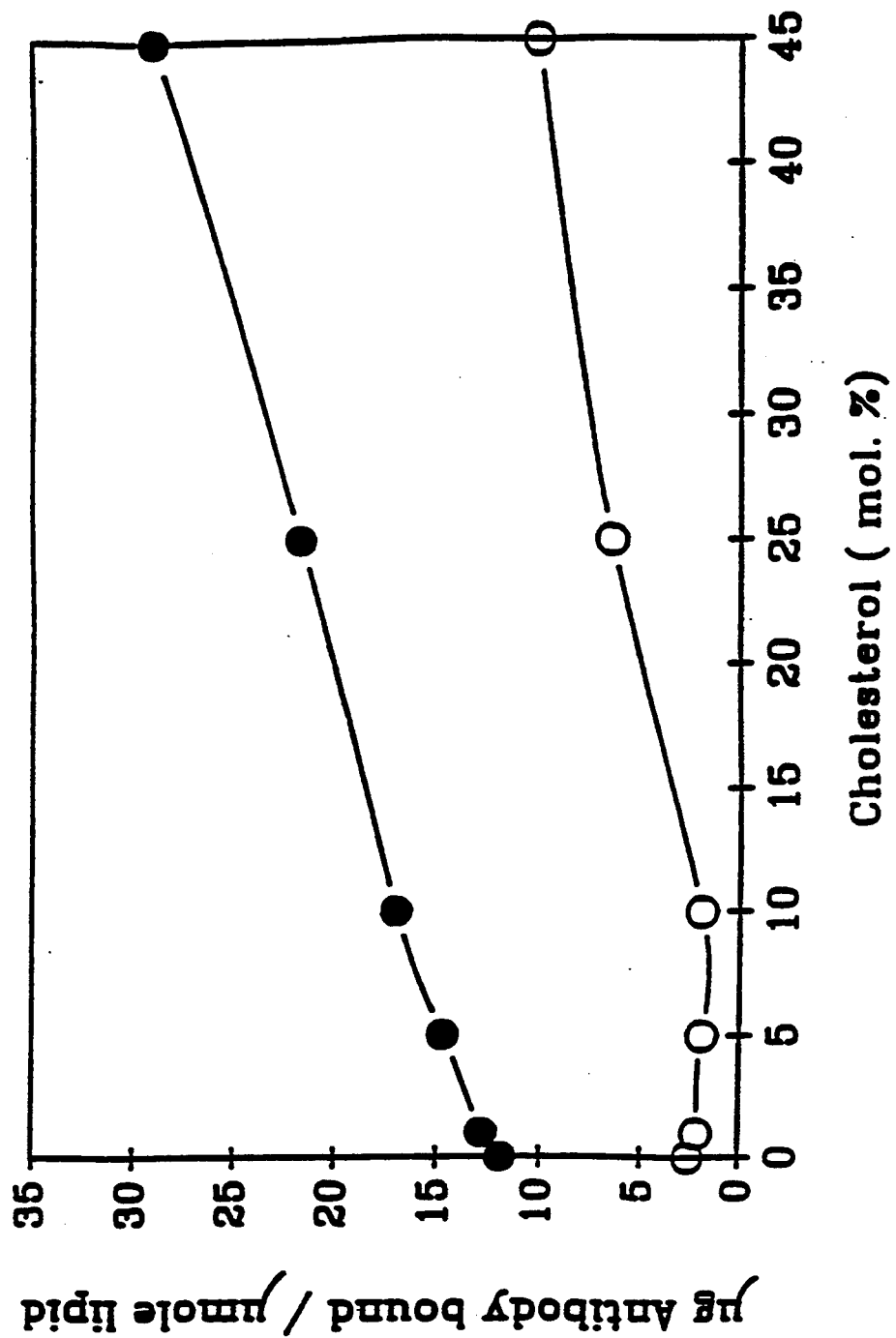
FIG. 1 shows the comparison of coupling of thiolated IgG to liposomes containing PDP-EPE and MPB-EPE as a function of the concentration of cholesterol included in the liposomes. As indicated, significant coupling of thiolated IgG to liposomes containing the PDP-EPE did not occur until greater than 20 mole % of cholesterol was incorporated into the liposomes. In stark contrast, levels of 12 ug IgG/umole of lipid were obtained for liposomes containing MPB-PE, even in the absence of cholesterol.

The present invention relates to an improved method of synthesizing a substantially pure reactive lipid, for example, MPB-PE, which may be incorporated into liposomes, and subsequently reacted with a protein, antibody, cofactor or other molecule to produce a conjugated liposome. The conjugated proteins of the present invention may be utilized for numerous targeting applications including bioactive agent delivery as well as targeting for diagnostic uses.

In the method of the present invention, a liposome forming nucleophilic lipid, for example, phosphatidylethanolamine (PE) is reacted with a crosslinking agent, for example, N-succinimidyl 4-(p-maleimidophenyl)butyrate (SMPB), to produce a substantially pure reactive lipid, for example, MPB-PE. In the method aspect of the present invention, the reaction of crosslinking agent and liposome forming nucleophilic lipid is performed in the presence of a non-nucleophilic solvent and optionally, a non-nucleophilic base, such as a tertiary amine. It has been discovered that the synthesis of MPB-PE by the prior art methods which utilize an alcoholic solvent in the presence of a non-nucleophilic base results in the production of substantial amounts of ring opened side product. This ring opened side product is significantly less reactive with thiol groups than is the maleimide group, resulting in the impure reactive lipid MPB-PE of the prior art being less efficient for coupling proteins, antibodies, cofactors and other molecules than is the MPB-PE of the present invention.

As used in the present invention, the crosslinking agents used to link conjugated molecules to reactive lipids are maleimide containing crosslinking agents, for example, those containing a p-maleimidophenylbutyrate group or other group, especially, for example, SMPB. Such agents are shown to be preferred reagents for cross-linking reactive liposomes and conjugated molecules, especially proteins. Although SMPB is a preferred reagent for use in the present invention, other agents containing maleimido groups may also be used. Among those crosslinking agents which may be used in the present invention include N-succinimidyl 3-maleimidobenzoate (SMB), N-succinimidyl 3-maleimidobutyrate (GMBS), N-succinimidyl 6-maleimidocaproate (EMCS), N-succinimidyl 3-maleimidopropionate, N-succinimidyl trans-4-(N-maleimidylmethyl)cyclohexane-1-carboxylate (SMCC) and N-succinimidyl maleimidylacetate (AMAS), among other maleimide containing crosslinking agents.

As used herein, the term liposome forming nucleophilic lipid refers to any lipid which may react with SMPB or an equivalent maleimide containing crosslinking agent to produce maleimido containing lipid or an equivalent lipid and which may be incorporated into liposomes with other liposome forming lipids. Such nucleophilic lipids include natural, synthetic and semi-synthetic lipids such as phosphatidylethanolamine, dipalmitoylphosphatidylethanolamine (DPPE), dimyristoylphosphatidylethanolamine (DMPE) and egg phosphatidylethanolamine (EPE), among others. In general, the more preferred nucleophilic lipids include those which contain an amine group, preferably a primary amine group, but other nucleophilic lipids including synthetic lipids containing alcoholic anions, such as oxy anions, among other nucleophilic groups, are also contemplated for use in the present invention. It will be recognized by those of ordinary skill in the art that the reactivities of the nucleophilic groups on the nucleophilic lipids and the amounts and concentrations of nucleophilic lipids and SMPB may be varied to produce pure reactive lipid. In general, it will be recognized that using more than a one to one molar ratio of nucleophilic lipid to SMPB may produce a maleimide ring opened side product.

The reaction to produce reactive lipid proceeds in a non-nucleophilic solvent. As used herein, the term non-nucleophilic solvent refers to any solvent having favorable characteristics of dissolving the reactive components, including, for example, a non-nucleophilic amine, but which itself does not produce a ring-opened side product. Examples of solvents which may be used in the method aspect of the present invention include chloroform, methylene chloride and higher chlorinated and halogenated solvents, dimethylsulfoxide (DMSO), dimethylformamide (DMF), dimethylacetamide (DMA), 1,4-dioxane, tetrahydrofuran (THF) and other ethers, among other solvents. Numerous other non-nucleophilic solvents may also be used in the present invention. It will be understood that the objectives in choosing a solvent for use in the present invention include maximizing the reaction to produce the reactive lipid and minimizing side products which are produced by the attack of solvent on the maleimide group of SMPB. It is to be recognized that the conditions of the prior art methods for producing reactive lipids are to be avoided and nucleophilic solvents such as methanol and ethanol, among other reactive alcohols, especially in the presence of base, are to be avoided.

It is important to note that in separating reactive lipid from displaced N-hydroxysuccinimide and other side products, the use of alcoholic and other nucleophilic solvents are to be avoided. Therefore, trituration or extraction techniques utilizing non-nucleophilic solvents are preferred for separating reactive lipids from more polar side products. As used herein, the term substantially pure reactive lipid refers to a reactive lipid in which the maleimido group is primarily intact, i.e., has not reacted with a nucleophile to produce a ring opened side product. The term substantially pure reactive lipid should not be interpreted to exclude reactive lipid having substantially intact maleimide groups but which also may contain minor impurities and side products other than ring opened side products.

The reactive liposomes of the present invention differ from prior art reactive liposomes in that the reactive liposomes of the present invention are substantially pure, i.e., they do not contain substantial amounts of ring-opened reactive lipid, for example, MPB-lipid. While not being limited by way of theory, such ring-opened reactive lipids are believed to affect the ability of the reactive liposome to form conjugated liposomes, and reactive liposomes containing appreciable amounts of ring opened reactive lipids markedly reduce the efficiency of a liposome to conjugate a protein or other molecule. This reduced efficiency plus the fact that reactive lipids tend to destabilize conjugated liposomes results in the reactive lipids and liposomes produced therefrom having significantly more favorable characteristics, including enhanced stability as well as enhanced binding characteristics, than the prior art conjugated liposomes.

After the substantially pure reactive lipid is isolated, it is incoporated into liposomes to produce reactive liposomes, i.e., liposomes that can further react with conjugated molecules such as proteins, antibodies, cofactors and other molecules to produce conjugated liposomes. Generally, the reactive liposomes comprise at least about 0.05 mole percent of a reactive lipid and at least about 90% by weight of a liposome forming lipid. Preferably, however, the amount of reactive lipid is no greater than about 2.5 mole percent of the total weight of the reactive lipid to promote the stability of the reactive liposome. The reactive liposome may be formed using virtually any method available in the art for forming liposomes, with care being exercised to avoid disrupting the reactive moiety, for example MPB, which functions to covalently bind to protein, antibody or cofactor to produce conjugated liposomes.

In general, after the reactive liposome is formed, a protein or other group is then bound to the reactive liposome through the maleimido group on the reactive lipid. Any protein, antibody, cofactor or related molecule may be bound to the maleimido group provided that such molecule is sufficiently nucleophilic, preferably containing a thiol group. Present studies conducted evidence that the thiol group is clearly preferred over other nucleophilic groups, for example, amine groups or alcohol groups and is much more reactive than other groups in the presence of preferred conditions of pH and temperature of the coupling reaction.

It is clearly preferred to bind a conjugated molecule which has some targeting function, i.e., will bind to some active site, receptor site or other binding site for purposes of delivering a bioactive agent or other molecule. Proteins which are useful in the present invention include streptavidin, various enzymes, immunomodulators, for example interleukin-1, interleukin-2, tumor necrosis factor (TNF), various peptides and peptide fragments, especially those for use in vaccination, antibodies, for example immunoglobulins such as IgG, IgM, IgE, monoclonal antibodies, and related proteins, among others. The present invention preferably contemplates the use of those proteins which covalently or non-covalently bind to the liposome and maintain their natural integrity so that, after binding to the reactive liposome, the protein may also bind to a target such as a receptor site, an antigenic determinant or other targeted binding site. Cofactors useful in the present invention especially include biotin because of its ability to non-covalently bind a number of proteins, including streptavidin and avidin.

Proteins useful in the present invention may be covalently linked to the reactive lipid of the reactive liposome, or alternatively, may be non-covalently linked to the reactive lipid through a cofactor, for example, biotin. Covalent linkages between the conjugated molecules and the reactive lipids may be formed by the reaction of thiol groups present in the protein or other molecule with the maleimido group of the reactive lipid. In cases where the conjugated molecule does not contain a thiol group, a thiol group may be introduced synthetically so that the molecule may be covalently linked to the liposome. In embodiments where the conjugated molecule is a protein, the protein may be modified with a bifunctional reagent, for example N-succinimidyl 3-(2-pyridyldithiol) propionate (SPDP) to produce a protein containing two thiol groups which may react with the maleimido group of the reactive lipid.

Bifunctional reagents useful to modify a conjugated molecule for binding to the reactive lipid include those agents which contain at least one group which is reactive with the conjugated molecule and at least one group reactive with the maleimido group of the reactive lipid. A large number of bifunction reagents are useful in the present invention as indicated hereinabove, for example, SPDP, succinimidylacetylthioacetate (SATA) and succinimidylacetylthioproprionate (SATP) among others.

In another aspect of the present invention, the conjugated molecule, for example, protein may first be covalently linked to a cofactor, for example, biotin before the protein is covalently linked to the reactive lipid. In this aspect of the invention where biotin is employed, a protein such as streptavidin may be reacted with N-hydroxysuccinimide biotin or p-nitrophenyl biotin to produce a covalently biotinated protein for use in producing the protein-liposome conjugate.

In another aspect of the present invention, the protein-liposome conjugates containing streptavidin or other biotin-binding protein can be further coupled to proteins such as IgG or monoclonal antibodies which have been biotinated by coupling to biotin with, for example, N-hydroxysuccinimide biotin. Quite surprising is the observed stability of the protein-liposome conjugates which makes the proteins an attractive coupler between the liposomes and the target sites.

In the aspect of the present invention in which protein is non-covalently bound to the reactive liposome, the liposomes are first formed utilizing most preferably between about 0.1 mole percent and about 1 mole percent of a reactive lipid, for example phosphatidylethanolamine, covalently linked to a maleimide containing crosslinking agent which will react with a cofactor or modified cofactor. A preferred example of a cofactor to which certain proteins, for example, avidin and streptavidin will readily bind is biotin. In certain aspects of the present invention where biotin is used, biotin may be introduced onto MPB-PE by modifying the biotin to contain a thiol group which then covalently binds to MPB-PE to produce a conjugated liposome containing biotin. A protein such as streptavidin may be non-covalently bound to the biotin of the conjugated liposome.

When protein is covalently or non-covalently linked to liposomes to produce protein-liposome conjugates, the liposomes may aggregate and increase in size. In such cases, it may be preferable to extrude the liposomes to produce sized liposome conjugates. Methods for producing sized liposomes to reduce aggregation are available in the art and have been previously described in U.S. patent application Ser. No. 370,650, entitled "Preparation of Targeted Liposome Systems of a Defined Size Distribution," filed Jun. 23, 1989 which is incorporated by reference herein.

In the method aspect of the present invention, the following steps are utilized:

1. SMPB is reacted with a nucleophilic lipid in a non-nucleophilic solvent for a period of time sufficient to complete the conversion of nucleophilic lipid to reactive lipid;
2. After complete conversion of nucleophilic lipid to reactive lipid, the solution is concentrated in vacuo and the solid residue is triturated with solvent to remove unreacted SMPB and displaced succinimide to produce a substantially pure reactive lipid, for example, MPB-PE.

Preferably, an extraction step is employed in the reaction after step 1 to remove byproducts such as N-hydroxysuccinimide. In that step, the reaction mixture from step 1 may be diluted with a non-nucleophilic solvent and then washed several times to remove byproducts. After the extraction step is performed, step 2, above, the trituration step is generally performed.

One of ordinary skill in the art will recognize that various modifications of the above-identified reaction steps can be performed without departing from the invention of the present application, i.e., to produce substantially pure reactive lipid. For example, it will be recognized that instead of performing the trituration step (step 2, above), chromatographic separation employing non-nucleophilic solvents and conditions which avoid maleimide ring opening could be performed.

The present invention also relates to reactive liposomes incorporating substantially pure reactive lipids of the present invention. The reactive liposomes of the present invention comprise at least one substantially pure reactive lipid, for example, MPB-PE, in an amount sufficient to bind conjugated molecules, in combination with at least one additional liposome forming lipid. Reactive liposomes of the present invention generally comprise at least about 0.05 mole percent of a substantially pure reactive lipid such as MPB-PE in combination with at least one liposome forming lipid in an amount generally no greater than about 99.95 mole percent of the reactive liposome. A discussion of liposome forming lipids which may be used in the reactive liposomes and conjugated liposomes of the present invention is detailed hereinbelow.

The present invention also relates to enhanced methods for coupling proteins onto MPB-lipid containing reactive liposomes. It has been found that the reaction to bind protein to reactive liposome is most efficient when conditions of pH 7.5 and temperatures of about room temperature, i.e., 23° C. are employed. If one raises the pH or the temperature, the reaction will increase, but the integrity of MPB-PE will decrease. Likewise if one lowers the temperature or the pH, the coupling of protein to reactive liposome will decrease, resulting in less efficiency. The conditions of the present invention, i.e., temperatures of about 23° C. and a pH of about 7.5 are shown to produce the greatest efficiency of coupling of protein to reactive liposome to produce a protein conjugated liposome. In addition, the integrity of the reactive lipid is maximized under these conditions. Coupling efficiencies of over 50% are readily achieved under the optimized conditions of the method of the present invention. Similar efficiencies have been attained only on incorporation of higher levels of MPB-EPE in liposomes [5 mole %, see Bragman, et al., *J. Natl. Cancer Inst.*, 73, 127, (1984)].

The present invention also relates to liposome conjugates which result from the coupling of the liposomes to conjugated molecules such as proteins, antibodies, cofactors and other molecules. Such liposomes comprise an amount of a reactive lipid effective to bind conjugated molecules, an amount of a liposome forming lipid effective to form stable liposomes in combination with the reactive lipid and an amount of at least one conjugated molecule, for example, a protein, antibody, cofactor or other molecule, bound to the reactive liposome effective for targeting the liposome to a targeting site such as a receptor, active site or antigenic determinant.

The liposome conjugates of the present invention may be loaded with bioactive agent. In the case of liposome conjugates in which the conjugated molecule is a protein, such liposome conjugates may also be extruded to form sized liposomes to avoid aggregation of the liposomes. After the liposome conjugates of the present invention are formed, they may be dehydrated and rehydrated or alternatively, stored stably at 4° C. Alternatively, the liposome conjugates may be extruded to produce sized liposomes before they are loaded with bioactive agents. These liposome conjugates may be loaded with a chosen bioactive agent by potential difference of ions across the bilayer membranes after formation, during the rehydration step or subsequently thereto. Preferred methods for loading bioactive agents into liposomes include those disclosed by Madden, et al., in U.S. application Ser. No. 352,497, filed May 15, 1989, entitled "Accumulation of Drugs Into Liposomes by a Proton Gradient" relevant portions of which are incorporated by reference herein. Alternatively, the bioactive agent may be added to the liposome conjugates prior to dehydration.

The liposome conjugates of the present invention may be administered to a subject, for example a mammal including humans. The composition may be delivered to such a subject parenterally in a pharmaceutically acceptable carrier or diluent such as phosphate buffered saline. The proteins bound to the liposomes aid in targeting the liposomes and their contents to a specific site in the body. When used parenterally as in the case of bioactive agents such as antineoplastic agents, the amount used will be determined by the physician, and the treatment procedure as determined by the size of the tumor or other condition.

The liposome conjugates of this invention may also be used in diagnostic assays; in this case the amount of the liposome conjugate used will depend on the sensitivity of the liposome-coupled antibody to the target components in the sample.

In certain preferred embodiments, the reactive liposomes used to form liposome conjugates are themselves formed using the LUVET apparatus described in copending U.S. patent application entitled "Extrusion Technique for Producing Unilamellar Vesicles" Ser. No 622,690, filed Jun. 20, 1984, relevant portions of which are incorporated herein by reference, and coupled to strepavidin using a modified technique of Leserman et.al., (*Liposome Technology, III,* 1984, CRC Press, Inc., New York, p. 29-40). Liposomes may be formed with a transmembrane potential i.e., a Na+/K+ or H+ gradient across the bilayers, see copending U.S. patent application Ser. No. 749,161, Bally et.al., entitled "Encapsulation of Antineoplastic Agents in Liposomes", filed Jun. 26, 1985, relevant portions of which are incorporated herein by reference; this potential difference is effected by the ionic concentrations of the internal versus the external media of the liposome. After loading the liposomes with bioactive agent, the liposomes are then dehydrated either in the presence or absence of sugars such as trehalose, and may be stored in this state for indefinite periods of time; see copending U.S. patent application Ser. No. 759,419, Janoff et.al., entitled "Dehydrated Liposomes," filed Jul. 26, 1985, relevant portions of which are incorporated herein by reference.

The reactive liposomes used in the present invention can have a variety of compositions and internal contents, and can be in the form of multilamellar, unilamellar, or other types of liposomes, or more generally, lipid-containing particles, now known or later developed. For example, the lipid-containing particles can be in the form of steroidal liposomes, stable plurilamellar liposomes (SPLVs), monophasic vesicles (MPVs), or lipid matrix carriers (LMC) of the types disclosed in commonly assigned U.S. patent applications Ser. Nos. 476,496, 521,176, 591,576 and 599,691, filed Mar. 24, 1983, Aug. 8, 1983, Mar. 20, 1984, and Apr. 12, 1984, respectively, the pertinent portions of which are incorporated herein by reference. However, it is to be recognized that the liposome should comprise at least about 0.1 mole percent and preferably no greater than about 10 mole percent of a reactive lipid as herein defined.

Liposome forming lipids which can be used in the liposomes of the present invention include synthetic, semi-synthetic or natural phospholipids and may include phosphatidylcholine (PC), phosphatidylethanolamine (PE), phosphatidylserine (PS), phosphatidylglycerol (PG), phosphatidic acid (PA), phosphatidylinositol(PI), sphingomyelin (SPM) and cardiolipin, among others, including hydrogenated phopholipids, either alone or in combination. The phospholipids useful in the present invention may also include dimyristoylphosphatidylcholine (DMPC) and dimyristoylphosphatidylglycerol (DMPG). In other embodiments, distearylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used. Due to the elevated transition temperaturres ($T_c$) of lipids such as DSPC ($T_c$ of about 65° C.), DPPC ($T_c$ of about 45° C.) and DAPC ($T_c$ of about 85° C.), such lipids are preferably heated to about their $T_c$ or temperatures slightly higher, e.g., up to about 5° C. higher than the $T_c$, in order to make these liposomes. In preferred embodiments, egg phosphatidylcholine is used.

In a number of embodiments of the present invention, a steroidal component may be added to the liposome. For purposes of the present invention any component including the above-described phospholipids which may be used to produce a liposome either alone or in combination with a phospholipid is termed a liposome forming lipid. In preferred embodiments of the present invention, the liposome forming lipid (non-nucleophilic) comprises at least about 90 mole percent of the total weight of lipids of the liposome. Any of the above-mentioned phospholipids may be used in combination with at least one additional component selected from the group consisting of cholesterol, cholestanol, coprostanol or cholestane. In addition, polyethylene glycol derivatives of cholesterol (PEG-cholesterols), as well as organic acid derivatives of sterols, for example cholesterol hemisuccinate (CHS) may also be used in combination with any of the above-mentioned phospholipids. Organic acid derivatives of alpha-tocopherol hemisuccinate, (THS) may also be used. CHS- and THS-containing liposomes and their tris salt forms may generally be prepared by any method known in the art for preparing liposomes containing sterols, so long as the resultant phospholipid-sterol mixture yields stable liposomes which may be cross-linked with protein. In particular, see the procedures of Janoff, et al., U.S. Pat. No. 4,721,612, issued Jan. 26, 1988, entitled "Steroidal Liposomes", and Janoff, et al., PCT Publication No. 87/02219, published Apr. 23, 1987, entitled "Alpha Tocopherol-Based Vehicles", relevant portions of which are incoporated by reference herein. In preferred embodiments cholesterol is utilized in combination with EPC in a weight ratio of cholesterol to EPC of about 45:555.

Techniques used for producing large unilamellar liposomes (LUVs), such as, reverse-phase evaporation, infusion procedures, and detergent dilution, can be used to produce the reactive liposomes. A review of these and other methods for producing liposomes can be found in the text *Liposomes*, Marc J. Ostro, ed., Marcel Dekker, Inc., New York, 1983, Chapter 1, the pertinent portions of which are incorporated herein by reference.

Several extrusion methods may be used to produce reactive liposomes or alternatively, liposome conjugates of the present invention. To produce reactive liposomes, MLVs may be extruded through filters forming large unilamellar vesicles (LUVs) of sizes dependent upon the filter size utilized. In general, polycarbonate filters of 30, 50, 60 or 100 nm pores may be used to produce sized liposome conjugates of the present invention, for example, using the techniques and as disclosed in U.S. patent application Ser. No. 370,650, entitled "Preparation of Targeted Liposome Systems of a Defined Size Distribution," filed Jun. 23, 1989 which is incorporated by reference herein. In one method to produce sized liposomes, as disclosed in Cullis, et al., PCT Publication No. WO 86/000238, Jan. 16, 1986, relevant portions of which are incorporated by reference herein, the liposome suspension may be repeatedly passed through the extrusion device resulting in a population of liposomes of homogeneous size distribution. For example, the filtering may be performed through a straight-through membrane filter (a Nucleopore polycarbonate filter) or a tortuous path filter (e.g. a Nucleopore filter membrafil filter (mixed cellulose esters) of 0.1 um size), or by alternative size reduction techniques such as homogenization. Although the size of the reactive liposomes may vary from about 30 to above about 200 nm in diameter, preferably, the reactive liposomes are about 100 nm to about 200 nm in size. Generally, sized liposome conjugates range in size between about 75 nm and about 200 nm.

As described hereinabove, a number of liposome forming lipids may be used to form reactive liposomes having a gel to liquid crystalline $T_c$ above ambient temperature. In such cases, an extruder having a heating barrel or thermojacket may be employed. Such a device serves to increase the liposome suspension temperature allowing extrusion of the LUVs. The lipids which are used with the thermojacketed extruder are, for example, DSPC, DPPC, DMPC and DAPC or mixtures thereof, which may include cholesterol in certain embodiments. Liposomes containing DSPC are generally extruded at about 65° C., DPPC at about 45° C. and DAPC at about 85° C. (about 5° C. above the lipid $T_c$).

After extrusion, the reactive liposomes or liposome conjugates may be loaded with bioactive agent or dehydrated for storage. However, in the case of liposome conjugates, some loss of bioactive agent may result during the extrusion step. To avoid this possible result, it is preferred to load the bioactive agent after extrusion. The liposomes and liposome conjugates of the present invention may be dehydrated using standard freeze-drying equipment or equivalent apparatus, and, if desired, the liposomes or liposome conjugates and their surrounding medium can be frozen in liquid nitrogen before being dehydrated. Alternatively, the liposomes and liposome conjugates can also be dehydrated without prior freezing, by simply being placed under reduced pressure. Dehydration with prior freezing requires the presence of one or more protective sugars in the preparation. A variety of sugars can be used, including such sugars as trehalose, maltose, sucrose, glucose, lactose, and dextran. In general, disaccharide sugars have been found to work better than monsaccharide sugars, with the disaccharide sugars trehalose and sucrose being most effective.

The one or more sugars are included as part of either the internal or external media of the liposomes or protein-lipsome conjugates. Most preferably, the sugars are included in both the internal and external media so that they can interact with both the inside and outside surfaces of the liposomes' and liposome conjugates' membranes. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, e.g., to create a transmembrane potential (see below), the new external medium should also include one or more of the protective sugars.

In the case of dehydration without prior freezing, if the liposomes and liposome conjugates being dehydrated have multiple lipid layers and if the dehydration is carried out to an end point where there is sufficient water left in the preparation so that a substantial portion of the membranes retain their integrity upon rehydration, the use of one or more protective sugars may be omitted. It has been found preferable if the preparation contains at the end of the dehydration process at least about 2%, and most preferably between about 2% and about 5%, of the original water present in the preparation prior to dehydration.

Once the liposomes or liposome conjugates have been dehydrated, they can be stored for extended periods of time until they are to be used. When the dehydrated liposomes or liposome conjugates are to be used, rehydration is accomplished by simply adding an aqueous solution, e.g., distilled water, to the liposomes or liposome conjugates and allowing them to rehydrate.

As discussed hereinabove, the liposomes and liposome conjugate preparation of the present invention may be loaded with ionizable pharmacological agents, for example antineoplastic agents, wherein a transmembrane potential is created across the bilayers of the liposomes or liposome conjugates and the antineoplastic agent is loaded into the liposomes by means of the transmembrane potential. The transmembrane potential is generated by creating a concentration gradient for one or more charged species (e.g., $Na+$, $K+$ and/or $H+$) across the liposome membranes. The concentration gradient is created by producing liposomes and liposome conjugates having different internal and external media, i.e., internal and external media having different concentrations of one or more charged species.

Specifically, reactive liposomes used to produce the liposome conjugates of the present invention are prepared which encapsulate a first medium having a first concentration of the one or more charged species. For a typical liposome preparation technique (see discussion above), this first medium will surround the liposomes as they are formed, and thus the liposomes' original external medium will have the same composition as the first medium. To create the concentration gradient, the original external medium is replaced by a new external medium having a different concentration of the one or more charged species. The replacement of the external medium can be accomplished by various techniques, such as, by passing the liposome preparation through a gel filtration column, e.g., a Sephadex column, which has been equilibrated with the new medium, or by centrifugation, dialysis, or related techniques.

In accordance with the invention, it has been found that this transmembrane potential can be used to load ionizable antineoplastic agents into the liposomes or alternatively, into the sized liposome conjugates. Specifically, once liposomes having a concentration gradient and thus a transmembrane potential of the appropriate orientation have been prepared, the process of loading pharmaceutical agents into the liposomes reduces to the very simple step of adding the agent to the external medium. Once added, the transmembrane potential will automatically load the agent into the liposomes.

The transmembrane potential loading method can be used with essentially any pharmacological agent, including antineoplastic agents, which can exist in a charged state when dissolved in an appropriate aqueous medium (e.g., organic compounds which include an amino group which can be protonated). Preferably, the agent should be relatively lipophilic so that it will partition into the liposome membranes. Examples of some of the pharmacological agents which can be loaded into liposomes by this method include antineoplastic agents, for example, doxorubicin, mitomycin, bleomycin, daunorubicin, streptozocin, vinblastine, vincristine, mechlorethamine hydrochloride, melphalan, cyclophosphamide, triethylenethiophosphoramide, carmustine, lomustine, semustine, fluorouracil, hydroxyurea, thioguanine, cytarabine, floxuridine, decarbazine, cisplatin and procarbazine; local anaesthetics, for example, lidocaine, dibucaine and chlorpromazine; bronchodilators, for example, metaproterenol, terbutaline and isoproterenol; beta-adrenergic blockers, for example propanolol, timolol and labetolol; antihypertensive agents, for example clonidine and hydralazine; anti-depressants, for example, imipramine, amitryptyline and doxepim; anti-convulsants, for example, phenytoin; anti-emetics, for example, procainamide and prochlorperazine; antihistamines, for example, diphenhydramine, chlorpheniramine and promethazine; anti-arrhythmic agents, for example, quinidine and disopyramide; anti-malarial agents, for example, chloroquine, quinacrine and quinine; and analgesics, among a number of additional pharmaceutical agents.

In addition to loading a single pharmacological agent, the method can be used to load multiple pharmacological agents, either simultaneously or sequentially. Also, the liposome conjugates into which the ionizable antineoplastic agents are loaded can themselves be preloaded with other antineoplastic agents or other drugs using conventional encapsulation techniques (e.g., by incorporating the drug in the buffer from which the liposomes are made).

It has been found that the rate of release of a pharmacological agent can be markedly reduced by creating a transmembrane potential across the liposome conjugate membranes which is oriented to retain the agent within the conjugate. That is, for an agent which is positively charged when ionized, a transmembrane potential is created across the liposome conjugate membranes which has an inside potential which is negative relative to the outside potential, while for an agent which is negatively charged, the opposite orientation is used.

As with the transmembrane loading aspects of the invention, the transmembrane potentials used to reduce the rate of drug release are created by adjusting the concentrations on the inside and outside of the liposomes or liposome conjugates of a charged species such as $Na+$, $K+$ and/or $H+$. Indeed, if the liposomes or liposome conjugates have been loaded by means of a transmembrane potential produced by such a concentration gradient, simply keeping the liposomes or liposome conjugates in an external medium which will maintain the original concentration gradient will produce the desired reduction in the rate of release. Alternatively, if a transmembrane potential has not already been created across the liposome or liposome conjugates membranes, e.g., if the liposomes or liposome conjugates have been loaded using a conventional technique, the desired transmembrane potential can be readily created by changing the composition of the external medium using the exchange techniques described above.

In the method aspect of the invention relating to dehydration of the liposome conjugates, two basic approaches are provided. In the first approach, the conjugates can be loaded with bioactive agents (e.g., using conventional techniques or the transmembrane potential loading technique described above), dehydrated for purposes of storage, shipping, and the like, and then rehydrated at the time of use. Alternatively, pre-formed liposome conjugates can be dehydrated for storage, etc., and then at or near the time of use, rehydrated and loaded with an ionizable bioactive agent using the transmembrane potential loading technique described above.

When the dehydrated liposome conjugates are to be used, rehydration is accomplished by simply adding an aqueous solution, e.g., distilled water or an appropriate buffer, to the liposome conjugates and allowing them to rehydrate. The conjugates may be resuspended into the aqueous solution by gentle swirling of the solution. The rehydration can be performed at room temperature or at other temperatures appropriate to the composition of the liposomes and their internal contents.

If the bioactive agent which is to be administered is incorporated into the liposome conjugates prior to dehydration, and no further composition changes are desired, the rehydrated conjugates can be used directly in therapy following known procedures for administering liposome encapsulated drugs.

Alternatively, using the transmembrane potential procedures described above, ionizable bioactive agents can be incorporated into the rehydrated liposome conjugates just prior to administration. In connection with this approach, the concentration gradient used to generate the transmembrane potential can be created either before dehydration or after rehydration using the external medium exchange techniques described above.

Liposome conjugates having the same internal and external media, i.e., no transmembrane potential, can be prepared, dehydrated, stored, rehydrated, and then the external medium can be replaced with a new medium having a composition which will generate transmembrane potentials, and the transmembrane potentials used to load ionizable antineoplastic agents into the liposomes. Alternatively, liposome conjugates having internal and external media which will produce transmembrane potentials can be prepared, dehydrated, stored, rehydrated, and then loaded using the transmembrane potentials.

Liposome conjugates of the present invention may be administered to a subject such as a mammal, including humans. For administration to humans in the treatment of afflictions, the prescribing physician will ultimately determine the appropriate dose for a given human subject, and this can be expected to vary according to the age, weight, and response of the individual as well as the nature and severity of the patient's symptoms.

The mode of administration may determine the sites in the organism to which the compound will be delivered. For instance, delivery to a specific site of infection may be most easily accomplished by topical application (if the infection is external, e.g., on areas such as the eyes, skin, in the ears or on afflictions such as wound or burns) or by absorption through epithelial or mucocutaneous linings (e.g., nasal, oral, vaginal, rectal, gastrointestinal, mucosa, etc.). Such topical application may be in the form of creams or ointments. The liposome conjugate containing bioactive agent may be administered alone but will generally be administered in admixture with a pharmaceutical carrier selected with regard to the intended route of administration and standard pharmaceutical practice. The liposome conjugates of the present invention may be injected parenterally, for example, intravenously, intramuscularly, or subcutaneously. For parenteral administration, they are best used in the form of a sterile aqueous solution which may contain other solutes, for example, sufficient salts, glucose or dextrose to make the solution isotonic.

For the oral mode of administration, liposome conjugate compositions of the present invention can be used in the form of tablets, capsules, lozenges, troches, powders, syrups, elixirs, aqueous solutions and suspension, and the like. In the case of tablets, carriers which can be used include lactose, sodium citrate, and salts of phosphoric acid. Various disintegrants such as starch, and lubricating agents, for example, starch may be used. For oral administration in capsule form, useful diluents are lactose and high molecular weight polyethylene glycols. When aqueous suspensions are required for oral use, certain sweetening and/or flavoring agents can be added.

The liposome conjugates of the present invention may also be used in diagnostic assays; in this case the amount of the composition used will depend on the sensitivity of the liposome-coupled antibody to the target components in the sample.

The following examples are provided for purposes of illustration only and are not to be viewed as a limitation of the scope of the invention.

EXAMPLES

Materials and Methods

Egg phosphatidylcholine (EPC), egg phosphatidylethanolamine (EPE), and dipalmitoyal phosphatidylethanolamine (DPPE) were obtained from Avanti Polar Lipids (Birmingham, Ala. USA). N-succinimidyl 3-(2-pyridyldithio)propionate (SPDP), N-succinimidyl 4-(p-maleimidophenyl)butyrate (SMPB) were obtained from Molecular Probes, Oregon, USA and N-hydroxysuccinimide biotin (NHS-biotin) were obtained from Pierce Chemicals. Dithiothreitol (DTT), N-2-hydroxyethyl)-piperazine-N'-3-propanesulphonic acid (EPPS), 2-(N-morpholino)-ethanesulphonic acid (MES), N-2-hydroxyethylpiperazine-N'-2-ethanesulphonic acid (HEPES), FITC-cellite, ethylene diamine tetra-acetate (EDTA), dithiobis-2-nitrobenzoic acid (DTNB), N-ethylmaleimide (NEM), bovine serum albumin (BSA), carboxyfluorescein, streptavidin, biotinated-protein A, biotinated-alkaline phosphatase, biotinated-succinylated concanavalin A and sephadex G 50 were obtained from Sigma, USA. Anti-human erythrocyte IgG was purchased from Cappel, Inc. USA and biotinated anti-B 1 (PAN-B, IgG 2a) and biotinated anti-T 11 (E-rosette, IgG 1) were obtained from Coulter Electronics, USA. Sepharose CL-4B and ficoll paque were obtained from Pharmacia, N.J., USA. $^3H$ biotin was obtained from Amersham, N.J. USA and $^{14}C$ cholesterol was obtained from New England Nuclear, USA.

EXAMPLES 1 AND 2

Synthesis of
N-3[-(2-Pyridyldithio)propionyl-]phosphatidylethanolamine (PDP-PE) and
N-[4-(p-Maleimidophenyl)butyryl]phosphatidylethanolamine (MBP-PE)

PDP-EPE was synthesized as described by Leserman, et al., Nature (London), 288, 602 (1984). Briefly, 50 umole of EPE was dissolved in 3.5 ml chloroform/methanol (9:1) and added to 15 ml methanol containing 60 umole SPDP and 100 umole triethylamine. After a 4 hour incubation at room temperature, analysis by thin layer chromatography (TLC, running solvent: chloroform/methanol/water, 65:25:4) indicated 99% conversion of EPE to a faster running product. The reaction mixture was washed with 10 ml of phosphate buffered saline. This washing was repeated three times prior to removal of the organic phase under reduced pressure. Analysis by two dimensional TLC and proton NMR indicated a single product which was greater than 98% pure. PDP-PE was stored under nitrogen in chloroform at 20° C. for several months.

MBP-PE was initially synthesized according to the method of Martin, et al. (1982) with minor modifications. EPE (100 umole) was dissolved in 5 ml of anhydrous methanol containing 100 umole of freshly distilled triethylamine and 50 mg of SMPB. The reaction was carried out at room temperature under nitrogen and its progress monitored by TLC (running solvent: chloroform/methanol/water, 65:25:4). Following an 18 hour incubation, 95% of the EPE was converted to a faster running product. Methanol was removed under reduced pressure, the sample was dissolved in chloroform and washed extensively with 1% NaCl to remove unreacted SMPB and residual triethylamine. TLC analysis using the solvent system employed by Martin et al., *J. Biol. Chem.*, 257, 286 (1982) indicated that the lipid product ran as a single component which was ninhydrin-insensistive and phosphate positive. Further characterization of the reaction products by 2-dimension TLC (first dimension, base: chloroform/methanol/25% $NH_3/H_2O$, 90/54/5.7/5.3; second dimension, acid; chloroform/methanol/acetic acid/$H_2O$, 60/30/18/2.85) indicated the presence of two ninhydrin negative, phosphate positive lipid components ($R_f$ values in acid diminesion:0.93 and 0.783). These observations were confirmed by $^1H$ NMR analysis and the slower running product, which comprised approximately 60% of the total lipid fraction, was identified as pure MPB-DPPE.

The two thiol reactive lipids synthesized above, PDP-EPE and MPB-EPE were subjected to coupling reactions with thiolated IgG according to prior art methods to determine which of the two crosslinking groups was the more efficient. As shown in FIG. 1, sigificant coupling of thiolated IgG to liposomes containing PDP-EPE did not occur until greater than 20 mole % cholesterol was incorporated into liposomes. In contrast, levels of 12 ug IgG/umole lipid were obtained forliposomes containing MPB-EPE, even in the absence of cholesterol. The level of liposomally conjugated protein increased linearly with respect to amounts of cholesterol incorporated into vesicles. Significantly higher coupling ratios were obtained for the maleimide derivative of EPE under all conditions examined.

EXAMPLE 3

Synthesis of Pure MPB-PE

Pure MPB-DPPE was synthesized by reacting DPPE (69 mg) with SMPB (65 mg) in chloroform (5 ml) containing triethylamine (10 mg) at 40° C. After two hours, TLC on silica showed conversion of DPPE to a faster running product (solvent system: chloroform/methanol/acetonitrol/water, 75:16:5:4, Rf: 0.6). The solution was diluted with chloroform (10 ml) and washed several times with NaCl (0.9%) to remove by-products of the reaction. The solution was futher concentrated in vacuo and the solid residue was triturated and recrystallized from diethylether to remove unreacted SMPB. Further recrystallization from diethylether/acetonitrile yielded a pure product as indicated by $^1H$ NMR analysis (Bruker W40, 400 MHz). Fast Acting Bombardment (FAB) mass spectra were obtained at the British Columbia Regional Mass Spectroscopy Center, University of British Columbia, with AEI MS9.

EXAMPLE 4

Figure 3:
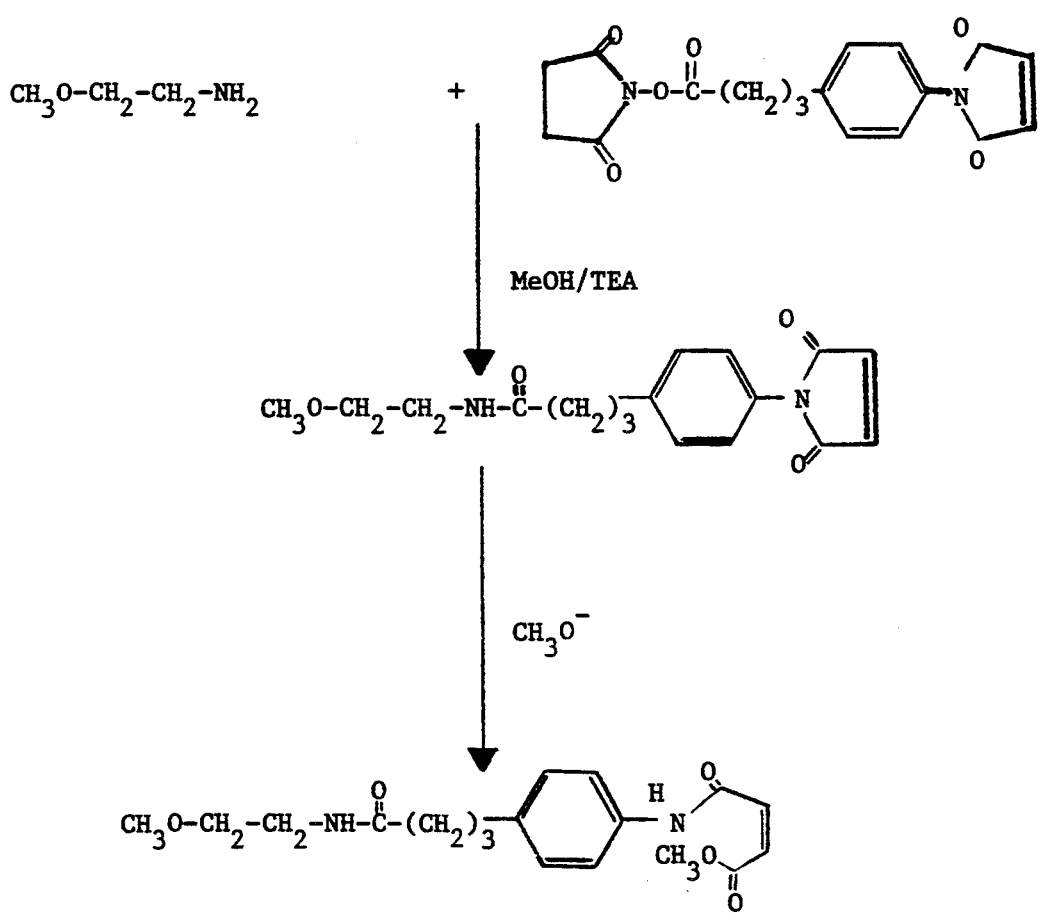
FIG. 3 presents a structural representation of the proposed reaction scheme of 2-methoxyethylamine (for purposes of determining the structure of ring-opened side product, the chemical equivalent of PE) with SMPB under conditions similar to those described in the prior art for synthesis of MPB-PE. The figure indicates that the reaction produces two products, one similar in structure to MPB-PE (Structure B) and the other product similar in structure to the ring-opened side product produced by methanolic attack on the keto group of the maleimido group.

Analysis of Reaction to Form MPB-PE $^1H$ NMR analysis of the tipid product obtained by reacting DPPE with SMPB according to Example 2 indicated the loss of the signal attributed to N-hydroxysuccinimide group of SMPB with the appearance of new peaks in the low field region of the $^1H$ NMR spectrum which were not characteristic of the expected product (delta: 7.58, 7.15 and 6.45, 6.22). In order to gain a better understanding of the conditions for the derivatization of DPPE with SMPB, 2-methoxyethylamine ($CH_3O$—$CH_2CH_2$—$NH_2$; FIG. 3, structure A) was selected as a model amine to react with SMPB.

The $^1H$ NMR spectrum of SMPB exhibits low filed resonances attributed to the aromatic protons of the phenyl group (chemical shift (delta):7.3 and vinyl protons (delta: 6.86), and high field resonances for methylenes of the N-hydroxysuccinimidyl group (NHS, delta: 2.86). When 2-methoxyethyleamine was incubated with SMPB under similar conditions described for the prior art synthesis of MPB-PE, two major products more polar than SMPB were detected by TLC (See FIG. 3 and Table 1, below). The less polar product was identified as the amide formed by the displacement of N-hydroxysuccinimide (NHS) from SMPB by $^1H$ NMR analysis due to the loss of a peak at delta 2.86 for the 4 methylene protons of the NHS group in SMPB and the appearance of new peaks at delta 3.35 (due to $OCH_3$) and delta 3.45 (due to O—$CH_2CH_2$; FIG. 3, structure B). Analysis of the more polar product by $^1H$ NMR revealed a pattern which was consistent with the ring opening of the maleimide group due to methanolysis of the ring structure (FIG. 3, Structure C). For example, as indicated in Table 1, the signals for the four aromatic protons appeared as two distinct doublets at delta 7.58 (d,J=8 Hz, two protons) while the resonances for the two vinyl protons shifted upfield and appeared as two doublets at delta 6.22 and delta 6.45 (J=13 Hz). The appearance of a sharp peak at delta 3.86 which integrated for three protons, was interpreted to arise due to the addition of methanol to the maleimide group, resulting in opening of the ring moiety.

These conclusions were further supported by mass spectrum analysis (structure B: molecular formula $C_{17}H_{20}N_2O_4$, molecular ion at 316; structure C: molecular formula $C_{18}H_{24}N_2O_5$, molecular ion at 348). Also $^1H$ NMR analysis of the MPB-DPPE lipid synthesized according to the prior art method of Martin, et al. indictaed the presence of a mixture of pure and ring open MPB-DPPE derivates in the sample.

Figure 2A:
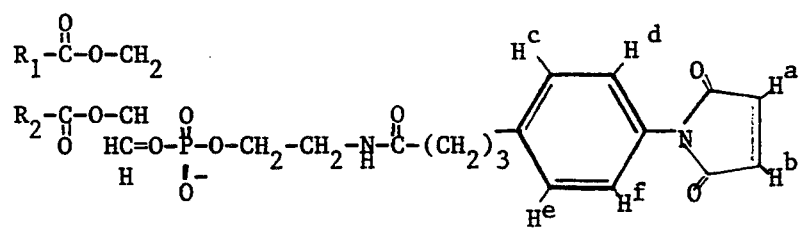
FIGS. 2 shows the NMR spectra of pure MPB-DPPE, which is synthesized by the method of the present invention.
Figure 2B:
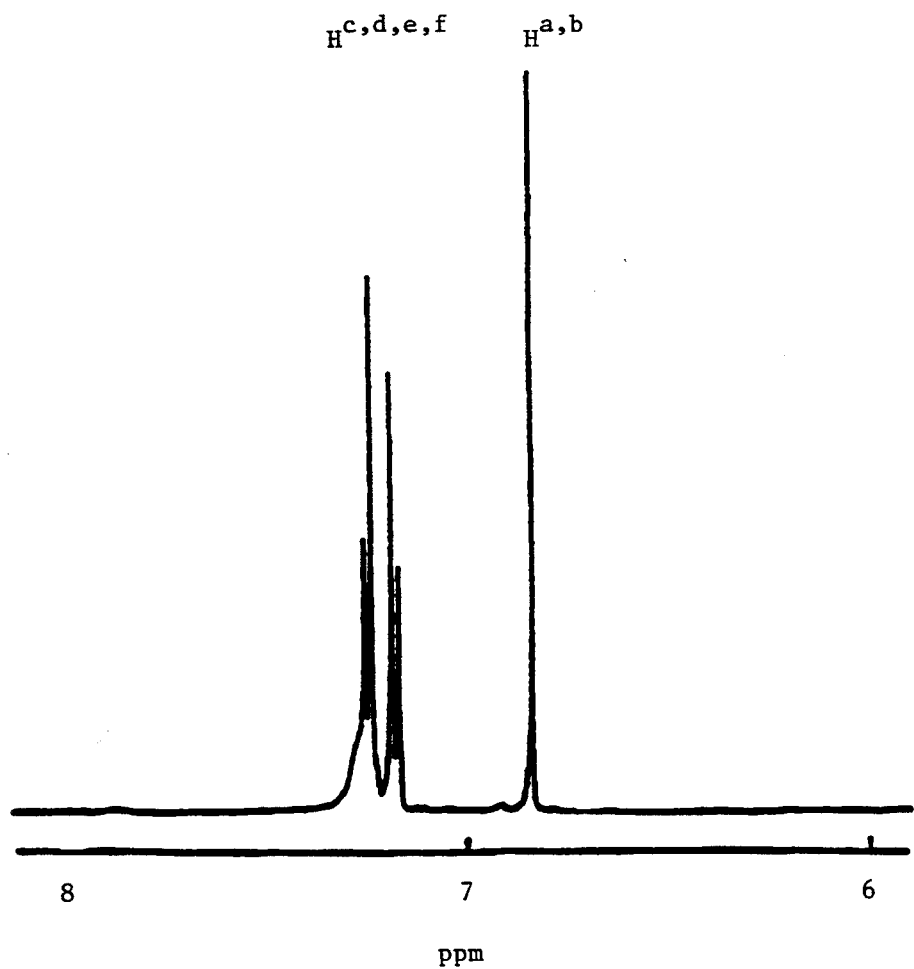

The susceptibility of the maleimide group to methanolic ring cleavage under basic conditions was confirmed by formation of a more polar product when a methanol solution of SMPB was treated with triethylamine (Table 1, below). As SMPB was found to be much more stable in chloroform, the derivatization of DPPE with SMPB was carried out in this solvent containing one equivalent of triethyleamine. The resulting lipid derivative was shown to be pure MPB-DPPE by $^1H$ NMR (FIG. 2). Mass spectroscopic analysis (FAB) confirmed the purity of the lipid derivative by the presence of a molecular ion at 955 which corresponded to a molecular formula of $C_{51}H_{84}O_{11}PNa$ for the sodium salt of MPB-DPPE.

TABLE 1
Summary of 1H NMR Chemical Shifts for SMPB and
SMPB derivates of 2-Methoxyethylamine (MEA) and DPPE

| SAMPLE | PHENYL PROTONS Intact d7.3 | PHENYL PROTONS Cleaved d7.58,7.15 | VINYL PROTONS Intact d6.86 | VINYL PROTONS Cleaved d6.45,6.22 | METHYLENES of NHS Group d2.86 |
|---|---|---|---|---|---|
| SMPB | X | | X | | X |
| SMPB + Methanol | | X | | X | |
| MPB-MEA | X | | X | | |
| MPB-MEA + Methanol | | X | | X | |
| MPB-DPPE (pure) | X | | X | | |
| MPB-DPPE + Methanol | | X | | X | |

EXAMPLE 5

Preparation of Liposomes

Large unilamellar vesicles (LUV's) were prepared as described by Hope, et al. (1985). Briefly, appropriate aliquots of lipid mixtures in chloroform were deposited in a tube and dried to a lipid film under a stream of nitrogen followed by high vacuum for two hours. Normally lipid samples (50–54% EPC, 45% cholesterol, 1–5% reactive lipid prepared according to examples 1–3) were hydrated in 150 mM NaCl, 25 mM HEPES, 25 mM MES, pH 6.5 and extruded 10 times through 2 stacked 100 nm filters. Just prior to coupling experiments, samples were titrated to the appropriate pH with NaOH. For studies on the thiol dependence of the coupling procedure, lipsomes containing 1% (for coupling) and 5% for maleimide reactivity pure MPB-DPPE were prepared at pH 6.5 as described above, titrated to pH 7.5 with NaOH and an aliquot was incubated with b-mercaptoethanol for 5 minutes at a molar ratio of 10 moles b-mercaptoethanol/mole of maleimide lipid. Liposomes were separated from free b-mercaptoethanol on sephadex G-50 equilibrated with 25 mM HEPES, 25 mM MES 150 mM NaCl, pH 7.5. The coupling efficiency potential and the reactivity of the maleimide group of quenched liposomes was comapared to that of unquenched samples. Lipid was estimated either by the colorimetric assay of Fiske and Subbarow, J. Biol. Chem., 66, 325 (1925) or by trace amounts of $^{14}C$ cholesterol present in the lipid mixture. This was performed by scintillation counting in a Packard Tri Carb liquid scintillation analyzer.

EXAMPLE 6

Assay for Maleimide Reactivity

Reactivity of the maleimide groups of MPB-PE lipids was estimated by the thiol binding of b-mercaptoethanol to lipid derivatives and back titration of unbound b-mercaptoethanol with Ellman's reagent, dithiobis-(2-nitro-benzoic acid) (DTNB) as described by Sedlack, et al., Anal. Biochem., 25, 192 (1968). Liposomes (5% MPB-DPPE, 50% EPC, 45% Cholesterol, 1 umole in 200 ul) were incubated with b-mercapoethanol (100 ul of 1 mM) at pH 8.2 (0.2M Tris Cl, 20 mM EDTA, 1% Triton-X-100, pH 8.2, 1.6 ml) for 30 minutes at room temperature. DTNB (100 ul, 20 mM in methanol) was added and the absorbance was measured at 412 nm after 30 minutes. The requirement for protein associated thiol groups in the coupling procedure is illustrated in Table 2, below. Prior exposure of MPB-DPPE liposomes to b-mercaptoethanol resulted in a decrease in the extent of lipsomally conjugated-streptavidin when quenched samples were compared to control MPB-DPPE. This was paralleled by a decrease in the detectable reactivity of the maleimide group of the lipid derivative. Futhermore, native streptavidin did not associate with liposomes containing the maleimide lipid.

TABLE 2

| SAMPLE | ug STREPTAVIDIN/ umole LIPID 8 HOURS | % MALEIMIDE REACTIVITY 0 HOURS | % MALEIMIDE REACTIVITY 8 HOURS |
|---|---|---|---|
| MPB-DPPE Liposomes | 36.0 | 100 | 73 |
| b-mercaptoethanol treated MPB-DPPE liposomes | 2.5 | 11 | 0 |
| MPB-DPPE liposomes + unthiolated streptavidin | 0 | 100 | 77 |

Results: Liposomes (1 or 5% MPB-DPPE, 54–50% EPC, 45% cholesterol) were quenched with b-mercaptoethanol (10 molar excess to MPB-DPPE) for 5 minutes at pH 7.5, exchanged on sephadex G-50 equilibrated with HBS pH 7.5 and incubated with streptavidin or alone (pH 7.5 for eight hours at room temperature). After 8 hours incubation, the extent of streptavidin conjugated to liposomes and the reactivity of the maleimide group was determined for control (unquenched MPB-DPPE liposomes or unthiolated streptavidin) and quenched samples. As indicated, in certain cases such as streptavidin, as with other proteins, the presence of reactive thiols greatly facilitates the coupling of protein onto reactive liposomes. In fact, in the case of streptavidin, the presence of thiol groups appears to be a necessity.

Separately, MPB-PE lipid synthesized by the prior art method of Martin, et al., supra, and MPB-PE synthesized by the method of the present invention were subjected to titration with b-mercaptoethanol at pH of 7.5. Liposomes (1 or 5% MPB-PE, 54–50% EPC, 45% cholesterol) were quenched with B-mercaptoethanol (10 molar excess to MPB-PE) for 5 minutes at pH 7.5, exchanged on sephadex G-50 equilibrated with HBS pH 7.5 and incubated with streptavidin or alone. After 8 hours of incubation, the extent of streptavidin conjugated to liposomes and the reactivity of the maleimide group was determined for control (unquenched) and quenched samples (see above). Pure MPB-PE produced greater quenching with b-mercaptoethanol than did the MPB-PE produced by the prior art methods. The absence of a large difference in the amount of streptavidin bound is probably the result of steric interactions hindering the thiol groups in streptavidin from reacting with maleimide. The results of this experiment appear in Table 3, below.

TABLE 3

Reactivity of MPB-PE with Mercaptoethanol pH 7.5

| SAMPLE | TREATMENT | ug Streptavidin umole Lipid 8 Hrs | % Maleimide Reactivity 0 Hrs | % Maleimide Reactivity 8 Hrs |
|---|---|---|---|---|
| RING OPEN | Nothing | 33.4 | 100 | 71 |
| MPB-PE | B-mercep. | 17.5 | 43 | 18 |
| INTACT | Nothing | 36.0 | 100 | 73 |
| MPB-PE | B-mercap. | 2.5 | 11 | 0 |

EXAMPLE 7

Preparation of Streptavidin and IgG for Coupling

In certain cases, as indicated above, in order to couple streptavidin protein to reactive liposomes containing MPB-PE, it is necessary to modify the protein to introduce reactive thiol groups.

Streptavidin (5 mg/ml in 25 mM HEPES, 150 mM NaCl, pH 7.5; HBS pH 7.5), was modified with the amine reactive reagent, SPDP according to the published procedurres of Carlsson, et al, Biochem. J., 173, 723 (1978). Briefly, SPDP (25 mM in methanol) was incubated at a 10 molar ratio to streptavidin at room temperature for 30 minutes. Unreacted SPDP was removed by gel filtration on sephadex G-50 equilibrated with HBS pH 7.5. PDP-modified streptavidin was reduced with DTT (25 mM, 10 minutes). The thiolated product was isolated by gel exclusion on sephadex G-50 equilibrated with the relevant buffer and was immediately used in coupling experiments. The extent of modification of streptavidin was determined by estimating the concentratio of the protein at 280 nm (extinction coeficient, $E_{280}$:2770) prior to the addition of dithiothreitol (DTT) and the 2-thiopyridone concentration at 343 nm ($E_{343}$:7550) 10 minutes after addition of DTT. In the case of IgG, after modification with SPDP as described for streptavidin, the protein was fluorescently labelled with FITC-cellite (50% weight of IgG, 20 minutes). Prior to the treatment of the protein with DTT, the sample was separted from unreacted regents on sephadex G-50 equilibrated with an acetate buffer (100 mM NaCl, 100 mM sodium acetate, pH 5.0) to protect against the reduction of the instrinsic disulfides of the molecule. Both protein preparations were modified to the same extent with SPDP (about 5–6 SPDP molecules per protein).

EXAMPLE 8

Coupling of Proteins to Liposomes

The coupling of proteins to liposomes was performed by incubating the reduced PDP-modified protein with liposomes containing PDP-PE, MPB-EPE or pure MPB-DPPE at a ratio of 100 ug protein/umole lipid (1 mM final concentration) at various pH values. Unassociated protein was removed by gel filtration on sepharose CL-4B equilibrated with HBS pH 7.5. The extent of coupling of streptavidin to liposomes was assayed by monitoring the binding of $^3$H biotin to streptavidin. Briefly, streptavidinliposomes (0.25 umole lipid in 0.5 ml) were incubated with $^3$H biotin (3.85 nmoles in 25 ul, 15.4 nmoles/uCi) for 10 minutes and unbound biotin was removed by gel exclusion on sepharose CL-4B equilibrated with HBS pH 7.5. The extent of $^3$H binding to a streptavidin sample (100 ug) after gel exclusion on sephadex G-50, was used as a reference for the calculation of coupling ratios. For the determination of the extent of antibody coupled to liposomes, samples (200 ul) were dissolved in ethanol (1.8 ml) and the liposome associated fluorescence was correlated to a known quantity of flurescein labelled antibody. Fluorescence was monitored at 520 nm using a SLM-aminco SPF-500C spectrofluoremeter with an excitation wavelength of 495.

EXAMPLE 9

Figure 4:
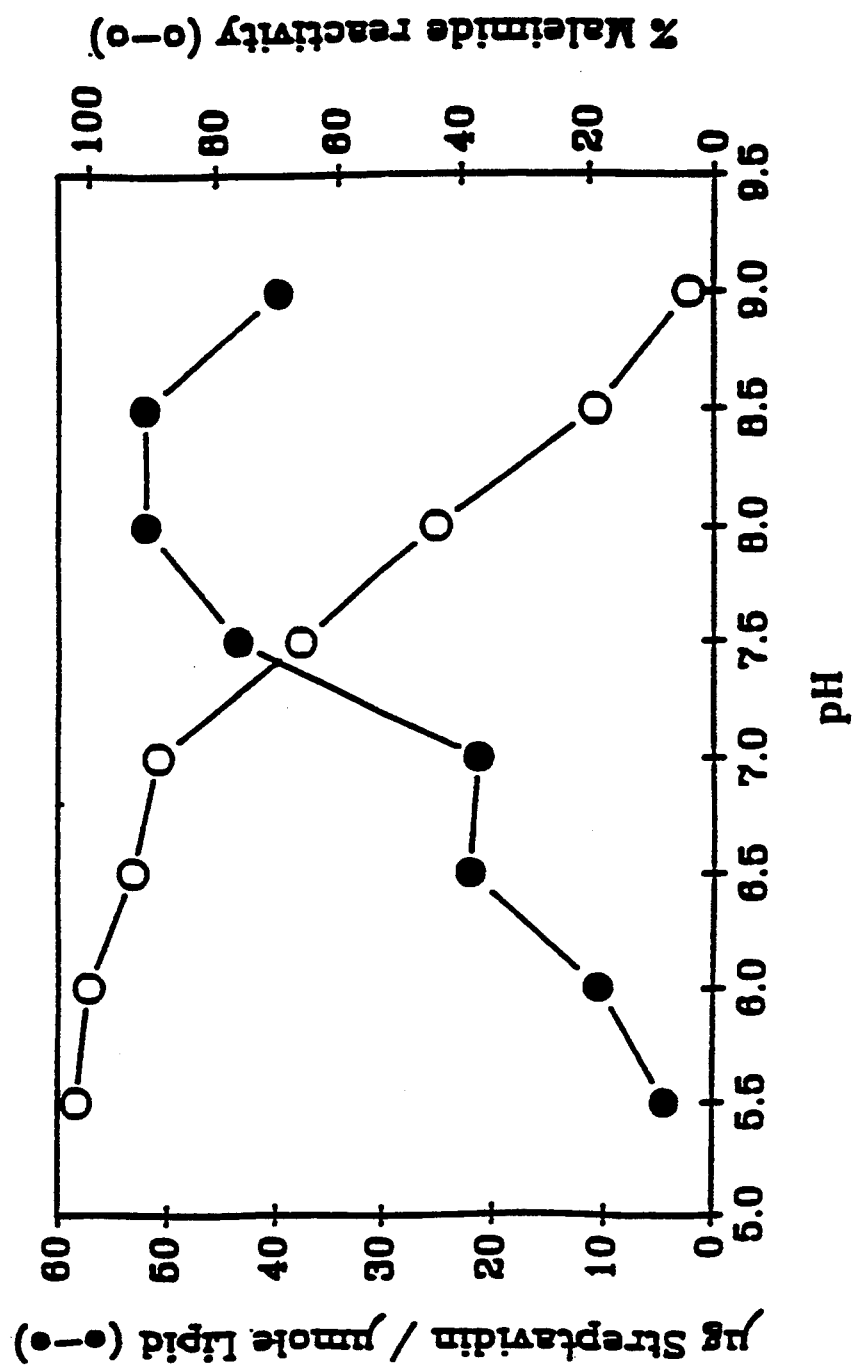
FIGS. 4 and 5 represent the investigation of the optimal conditions for coupling thiolated streptavidin to liposomes containing pure MPB-DPPE.

Optimal Conditions for Coupling Thiolated Streptavidin to Liposomes Containing Pure MPB-DPPE Optimal conditions for coupling thiolated streptavidin to liposomes containing pure MPB-DPPE were investigated. The results are presented in FIGS. 4 and 5. The pH dependence of the binding of thiolated streptavidin to MPB-DPPE liposomes and the stability of the maleimide function were initially established. As shown in FIG. 4, the amount of liposomally conjugated protein increased rapidly at pH values greater than 7.0. However, incubation of liposomes containing pure MBP-DPPE at pH values of 7.0 and above resulted in a corresponding rapid degradation of the maleimide group of the derivatized lipid. At pH 7.5 after 18 hours of incubation, significant levels of streptavidin were coupled to lipsomes (45%) with acceptable loss of maleimide reactivity (65% remaining). For this reason, a pH of 7.5 was chosen for further optimization of the coupling reaction.

Figure 5:
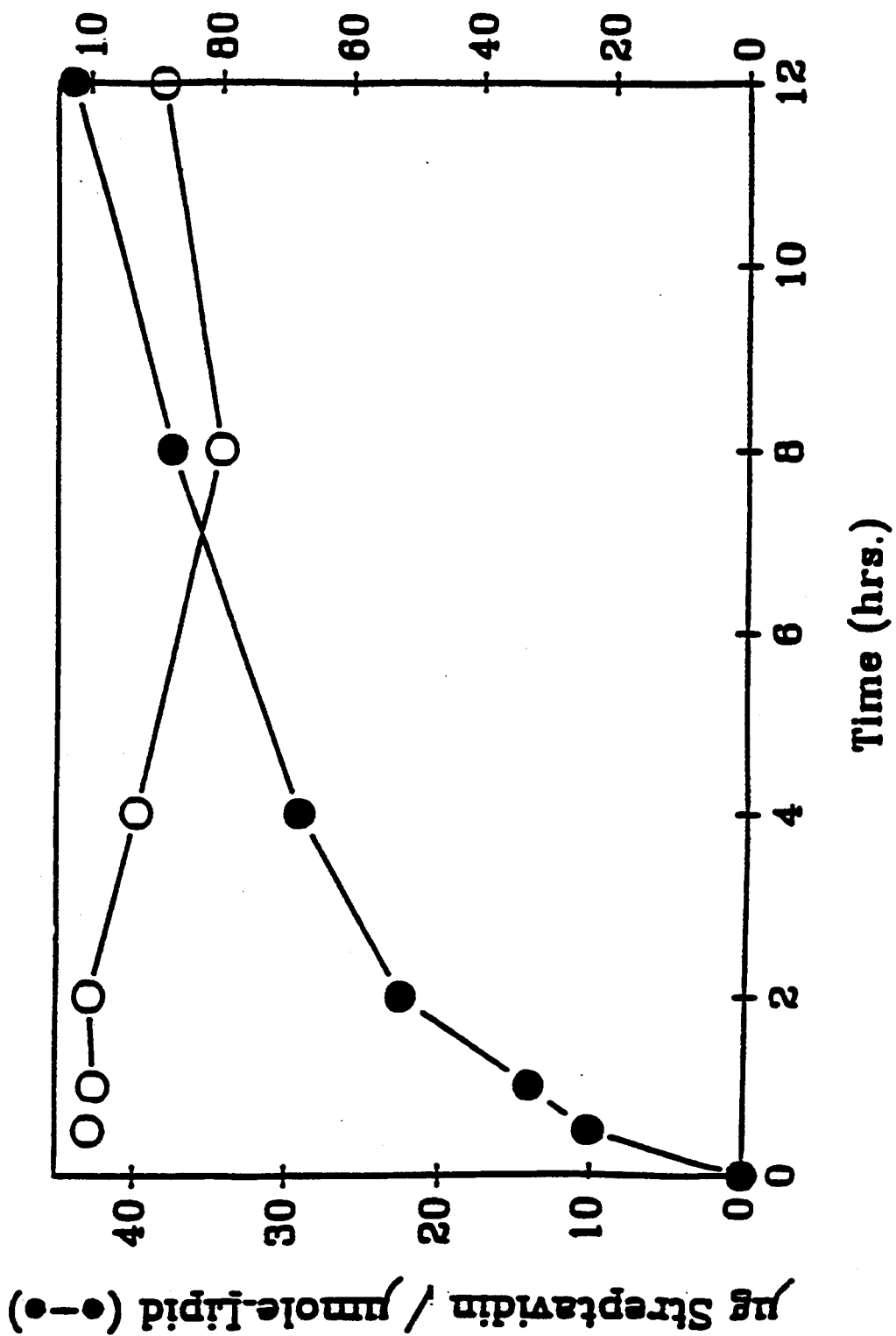

In FIG. 5, a time course relating streptavidin binding to liposomes and reactivity of the maleimide lipid is presented. The results indicate that optimal levels of streptavidin conjugated to liposomes (approximately 37 ug/umole of lipid) were obtained with minimal degradation of the maleimide group after an incubation period of 8 hours at pH 7.5 and at room temperature.

EXAMPLE 10

Applicability of Coupling to a Variety of Biotinated Proteins

To show the applicability of the general methodology of the present invention in attaching various types of targeting molecules to liposomes, the binding of a variety of biotinated proteins to streptavidin-liposomes was examined. As shown in Table 4, below, on incubation of various biotinated proteins with streptavidin conjugated liposomes, approximately 2 protein molecules bind for every 3 molecules of streptavidin. The extent of binding of biotinated proteins to streptavidin coupled vesicles is independent of the size of the biotinated protein (MW: 42,000–150,000 D). Briefly, streptavidin liposomes with 45.2 ug protein bound-/umole lipid were prepared as described in Example 8. Fluorescein labelled biotinated proteins were incubated with conjugated liposomes at a 2 fold molar excess to streptavidin for 10 minutes at pH 7.5. The extent of coupling of biotinated proteins to streptavidin lipsomes was determined after gel exclusion of samples on sepharose CL-4B by measuring the levels of fluorescence associated with lipsomes for protein and scintillation counting for lipid.

TABLE 4

Binding of Biotinated Proteins to Streptavidin Liposomes

| PROTEIN | ug/mole LIPID | nmole/umole LIPID | Molar Ratio Protein-Streptavidin |
|---|---|---|---|
| Anti-human Erythrocyte IgG (mw: 150 kD) | 62.6 | 0.417 | 1:1.68 |
| Alkaline Phosphatase (mw: 140 kD) | 77.7 | 0.555 | 1:1.25 |
| Protein A (mw: 43 kD) | 20.3 | 0.482 | 1:1.46 |
| Succinylated Con. A 26.4 (mw: 55 kD) |  | 0.480 | 1:1.46 |

EXAMPLE 11

Binding of Biotinated Proteins to Streptavidin-Liposomes

Anti-erythrocyte IgG was biotinated according to the method of Bayer, et al., FEBS Lett., 68, 240 (1976). All biotinated proteins were fluorescently labelled with FITC-cellite as described above for IgG. Proteins were incubated at a two fold molar ratio to streptavidin coupled to liposomes for 10 minutes. Unassociated protein was removed by gel exclusion on sepharose CL-4B pre-equilibrated with HBS pH 7.5. The extent of liposome associated protein was determined as described above for the fluorescently labelled IgG. Background binding of all biotinated proteins was shown to be negligible.

EXAMPLE 12

In Vitro Targeting of Streptavidin Liposome Conjugates

Liposomes with entrapped carboxyfluorescein (15 mM) were coupled to thiolated streptavidin as described above at pH 7.5 and a final lipid concentration of 2.5 mM. The coupling reaction was quenched with N-ethylmaleimide (500 molar ratio to streptavidin) after 4 hours, streptavidin liposome conjugates were isolated by gel exclusion on sepharose CL-4B and levels of liposomally associated streptavidin were determined as described above.

For targeting experiments, human blood was collected in EDTA (25 mM in PBS). Human peripheral blood leukocytes were isolated by standard protocols using Ficoll paque [see, Boyum, Scand. J. Clin. Lab. Invest., 21, Supp. 97, 9 (1968)] and suspended in PBS containing 2% BSA and 0.01% Na azide at 4° C. prior to binding studies. Cells ($10^6$) were aliquoted into round bottom microtitre wells, washed and incubated with antibody (T11 and B1, 5 and 10 ug respectively in 100 ul PBS) or alone in PBS for 1 hour at 4° C. After washing twice with PBS, cells were incubated with streptavidin liposome conjugates (0.2 umoles in 200 ul PBS) for a further hour at 4° C. The cells were then washed three times with PBS and analyzed by flow cytometry according to the procedure described below.

Briefly, cell associated fluorescence was measurred with an EPICS Profile analyzer (Coulter Electronics, Inc.). Cells were illuminated with the 488 nm line of an argon ion laser. Fluorescence was measured behind a 515 to 530 nm band-pass filter. Fluorescence signals were gated on the basis of a right angel versus forward light scatter cytogram to restrict analysis to signals from single cells. Amplifiers were set in the log area mode. For statistical analysis of histograms, region 1 was arbitrarily set (min.: 2.705, max.: 1023) with the lower channel at the base of the right shoulder of the histogram of the control sample.

Figure 6A:
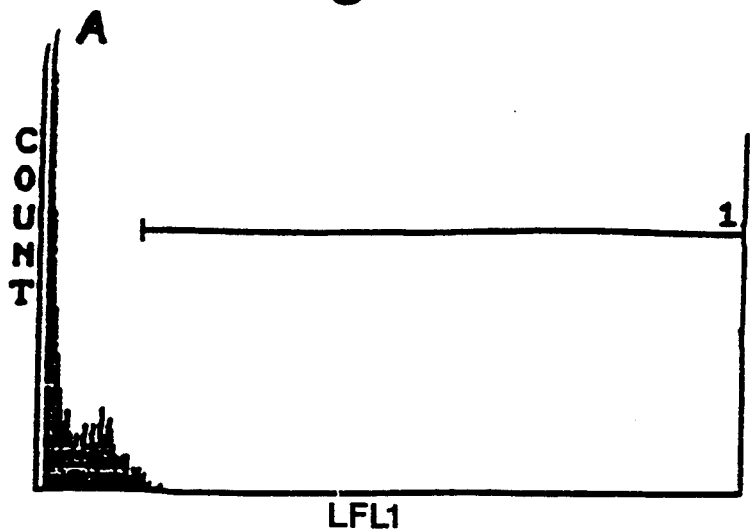
FIGS. 6A, B and C compare the targeting of liposomes to target cells through incubation of liposome streptavidin conjugates in the absence (FIG. 6A) or the presence of biotinated antibodies (FIGS. 6B and C) measured by flow cytometry techniques.
Figure 6B:
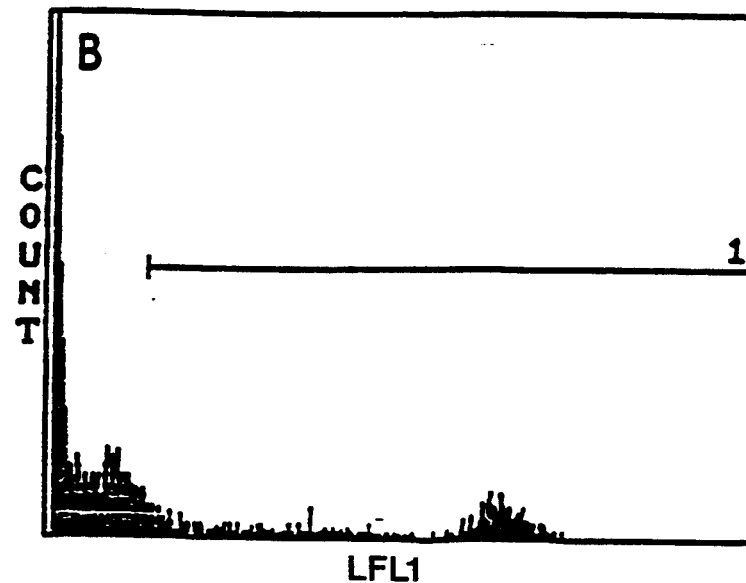
Figure 6C:
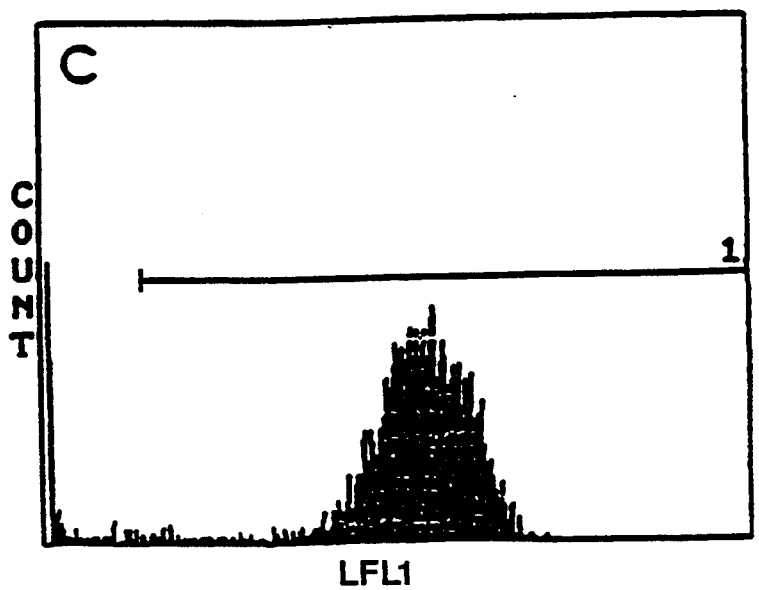

As show in FIG. 6, incubation of liposome streptavidin conjugates (containing encapsulated carboxyfluorescein) with cells pre-labelled with a biotinated monoclonal antibody specific for peripheral B cells (B1), resulted in the fluorescen labelling of approximately 20% of the total lymphocyte population (FIG. 6B). In comparison, similar studies with a biotinated anti T cell antibody (T11) resulted in the labelling of approximately 90% of lymphocytes (FIG. 6C). These results are consistent with the expected cell distribution of the antigens defined by T11 [See Howard, et al., J. Immunol., 126, 2117 (1981)] and B1 [See Stashenko, et al., J. Immunol., 125, 1678 (1980)]. The specificity of these conjugates is indicated by the negligible background binding of streptavidin liposomeconjugates to lymphocytes in the absence of biotinated antibodies (FIG. 6A).

It will be understood by those skilled in the art that the foregoing description and examples are illustrative of practicing the present invention, but are in no way limiting. Variations of the detail presented herein may be made without departing from the spirit and scope of the present invention.

We claim:

1. A conjugated liposome comprising the reaction product of:
   (a) a reactive liposome comprising an amount of a reactive lipid effective for binding a conjugated molecule and an amount of a liposome forming lipid effective for forming a liposome, wherein said reactive lipid is the reaction product of a nucleophilic lipid and a crosslinking agent having a maleimide moiety and wherein said liposome is substantially free of lipids bound to opened-ring maleimide moities; and
   (b) an amount of the conjugated molecule conjugated to said reactive liposome effective for therapeutic and diagnostic targeting.

2. The conjugated liposome according to claim 1 wherein said nucleophilic lipid is a phosphatidylethanolamine.

3. The conjugated liposome according to claim 2 wherein said nucleophilic lipid is dipalmitoyalphosphatidylethanolamine, dimyristoylphosphatidylethanolamine distearoyl phosphatidylethanolamine, dioleoyl phosphatidylethanolamine or egg phosphatidylethanolamine.

4. The conjugated liposome according to claim 1 wherein said crosslinking agent contains an N-[4-(p-maleimidophenyl)-butyryl] MPB group.

5. The conjugated liposome according to claim 4 wherein said crosslinking agent is N-succinimidyl 4-(p-maleimidophenyl)butyrate (SMPB).

6. The conjugated liposome according to claim 1 wherein said reactive lipid comprises the reaction product of a phosphatidylethanolamine with N-succinimidyl 4-(p-maleimidophenyl)butyrate (SMPB) in the absence of a nucleophilic alcohol.

7. The conjugated liposome according to claim 6 wherein said reactive lipid is substantially pure N-[4-(p-maleimidophenyl)-butyryl] dipalmitoylphosphatidylethanolamine (MPB-DPPE), N-[4-(p-maleimidophenyl)-butyryl] dimyristoylphosphatidylethanolamine (MPB- DMPE), or N-[4-(p-maleimidophenyl)-butyryl] egg phosphatidylethanolamine (MPB-EPE).

8. The conjugated liposome according to 1 wherein said reactive lipid comprises at least about 0.05 mole percent and said liposome forming lipid comprises no greater than about 99.95 mole percent of the lipid of said reactive liposome.

9. The conjugated liposome according to claim 1 wherein said conjugated molecule is selected from a protein, an antibody or a cofactor.

10. The conjugated liposome according to claim 9 wherein said protein is streptavidin.

11. The conjugated liposome according to claim 9 wherein said antibody is selected from the group consisting of IgG, IgM, IgE and monoclonal antibodies.

12. The conjugated liposome according to claim 9 wherein said cofactor is biotin.

13. The conjugated liposome according to claim 9 further comprising a protein noncovalently bound to said cofactor.

14. The conjugated liposome according to claim 13 further comprising streptavidin noncovalently bound to said biotin.

15. The conjugated liposome according to claim 1 wherein said conjugated liposome contains a bioactive agent.

16. The conjugated liposome according to claim 1 wherein said conjugated liposome has a transmembrane potential.

17. The conjugated liposome according to claim 16 wherein said conjugated liposome contains a bioactive agent.

18. The conjugated liposome according to claim 1 which is dehydrated.

19. The conjugated liposome according to claim 17 which is dehydrated.

20. The conjugated liposome according to claim 10 containing a bioactive agent.

21. The conjugated liposome according to claim 11 containing a bioactive agent.

22. The conjugated liposome according to claim 9 wherein said conjugated molecule is a protein and said conjugated liposome is a stable, sized liposome exhibiting an absence of aggregation.

23. A pharmaceutical composition comprising the conjugated liposome of claim 15 and a pharmaceutically acceptable carrier or diluent.

24. The composition according to claim 23 wherein said bioactive agent is an antineoplastic agent.

25. The composition according to claim 24 wherein said antineoplastic agent is selected from the group consisting of daunorubicin, doxorubicin, vinblastine, vincristine, cisplatinum, cyclophosphamide and pharmaceutically acceptable salts and mixtures, thereof.

* * * * *